US012622754B2

(12) United States Patent
McLeod et al.

(10) Patent No.: US 12,622,754 B2
(45) Date of Patent: May 12, 2026

(54) BEACON-BASED SYSTEMS, METHODS, AND APPARATUSES FOR MANAGING COMMUNICATIVE PAIRING OF AN APPARATUS WITH A MEDICAL SYSTEM

(71) Applicant: Intuitive Surgical Operations, Inc., Sunnyvale, CA (US)

(72) Inventors: A. Jonathan McLeod, Sunnyvale, CA (US); Mahdi Azizian, San Jose, CA (US); Alan S Bradley, Alameda, CA (US); Christopher R. Burns, San Jose, CA (US); Wen Pei Liu, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 387 days.

(21) Appl. No.: 18/280,012

(22) PCT Filed: Mar. 3, 2022

(86) PCT No.: PCT/US2022/018755
§ 371 (c)(1),
(2) Date: Sep. 1, 2023

(87) PCT Pub. No.: WO2022/187525
PCT Pub. Date: Sep. 9, 2022

(65) Prior Publication Data
US 2024/0138924 A1      May 2, 2024

Related U.S. Application Data

(60) Provisional application No. 63/157,226, filed on Mar. 5, 2021.

(51) Int. Cl.
*A61B 34/20* (2016.01)
*G16H 40/20* (2018.01)
*H04W 76/10* (2018.01)

(52) U.S. Cl.
CPC ............. *A61B 34/20* (2016.02); *G16H 40/20* (2018.01); *H04W 76/10* (2018.02);
(Continued)

(58) Field of Classification Search
None
See application file for complete search history.

(56) References Cited

U.S. PATENT DOCUMENTS

2019/0125456 A1      5/2019   Shelton, IV et al.
2020/0294392 A1      9/2020   Peesapati et al.

FOREIGN PATENT DOCUMENTS

EP            3069456 A1 *   9/2016   ............. H04B 11/00
JP          2020160589 A     10/2020
WO      WO-2021108437 A1 *   6/2021   ............. G16H 40/67

OTHER PUBLICATIONS

Zarandy, Almos; Shumailov, Ilia; & Anderson, Ross; "BatNet: Data Transmission Between Smartphones Over Ultrasound" (2020). (Year: 2020).*

(Continued)

*Primary Examiner* — Jason Holloway
*Assistant Examiner* — Bryant Tang

(57)      ABSTRACT

A first ultrasonic beacon transmission includes a first pilot signal and a first encoded information signal. An apparatus may detect the first pilot signal and decode, based on the first pilot signal, the first encoded information signal to identify a medical system associated with the first ultrasonic beacon transmission. Based on the first encoded information signal, the apparatus may enter into a first pairing state in which the apparatus is communicatively paired with the medical system. While the apparatus is operating in the first pairing state and within a threshold time of entering the first pairing state, the apparatus may detect a second pilot signal included in a second ultrasonic beacon transmission, which also includes a second encoded information signal. Based on the detection (Continued)

of the second pilot signal within the threshold time, the apparatus may continue operating in the first pairing state without decoding the second encoded information signal.

20 Claims, 14 Drawing Sheets

(52) U.S. Cl.
CPC ................. *A61B 2034/2048* (2016.02); *A61B 2034/2063* (2016.02); *A61B 2034/2072* (2016.02)

(56) References Cited

OTHER PUBLICATIONS

International Preliminary Report on Patentability for Application No. PCT/US2022/018755 mailed Sep. 14, 2023, 09 pages.
International Search Report and Written Opinion for Application No. PCT/US2022/018755, mailed May 31, 2022, 12 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

400

600

700

900

1100

BEACON-BASED SYSTEMS, METHODS, AND APPARATUSES FOR MANAGING COMMUNICATIVE PAIRING OF AN APPARATUS WITH A MEDICAL SYSTEM

RELATED APPLICATIONS

The present application is a U.S. National Stage Application under 35 U.S.C. § 371 of International Application No. PCT/US2022/018755, filed on Mar. 3, 2022, which claims priority to U.S. Provisional Patent Application No. 63/157,226, filed Mar. 5, 2021, the contents of which are hereby incorporated by reference in their entirety.

BACKGROUND INFORMATION

In a medical facility (e.g., a hospital, a nursing home, etc.), medical personnel may use a medical system to diagnose, treat, and/or assist patients. In some medical facilities the medical personnel may also use a user device (e.g., a tablet computer, a smartphone, etc.) in the diagnosis, treatment, and/or assistance of the patient. For example, during a computer-assisted surgical procedure, such as a minimally invasive surgical procedure performed at a surgical facility, a surgeon may interact with a computer-assisted surgical system to control teleoperated surgical instruments to perform the surgical procedure on a patient. Other surgical team members may also interact with the computer-assisted surgical system to assist with the surgical procedure. A surgical team member (e.g., a nurse) may use an auxiliary device (e.g., a mobile device) during the surgical procedure, such as to view information about the patient or the computer-assisted surgical system. There is a need to facilitate the use of an auxiliary device in conjunction with use of a medical system and to ensure that the auxiliary device receives and provides accurate and relevant information.

SUMMARY

The following description presents a simplified summary of one or more aspects of the methods and systems described herein in order to provide a basic understanding of such aspects. This summary is not an extensive overview of all contemplated aspects and is intended to neither identify key or critical elements of all aspects nor delineate the scope of any or all aspects. Its sole purpose is to present some concepts of one or more aspects of the methods and systems described herein in a simplified form as a prelude to the more detailed description that is presented below.

An illustrative apparatus may comprise one or more processors and memory storing executable instructions that, when executed by the one or more processors, cause the apparatus to detect a first pilot signal included in a first ultrasonic beacon transmission, the first ultrasonic beacon transmission further including a first encoded information signal; decode, based on the first pilot signal, the first encoded information signal to identify a first medical system associated with the first ultrasonic beacon transmission; enter, based on the decoding of the first encoded information signal, into a first pairing state in which the apparatus is communicatively paired with the first medical system; detect, while operating in the first pairing state and within a threshold time of entering the first pairing state, a second pilot signal included in a second ultrasonic beacon transmission, the second ultrasonic beacon transmission further including a second encoded information signal; and continue, based on the detection of the second pilot signal within the threshold time, operating in the first pairing state without decoding the second encoded information signal.

Another illustrative apparatus may comprise an ultrasonic sensor configured to detect ultrasonic signals; and a processing unit configured to determine that the ultrasonic sensor detects, while the apparatus is operating in a first pairing state in which the apparatus is communicatively paired with a first medical system, a first pilot signal included in a first ultrasonic beacon transmission, the first ultrasonic beacon transmission further including a first encoded information signal identifying a medical system associated with the first ultrasonic beacon transmission; determine that the ultrasonic sensor detects the first pilot signal within a threshold time of a pairing state initialization event; and control, based on the determination that the apparatus detects the pilot signal within the threshold time of the pairing state initialization event and without decoding the first encoded information signal, the apparatus to continue operating in the first pairing state.

An illustrative method may comprise detecting, by an apparatus, a first pilot signal included in a first ultrasonic beacon transmission, the first ultrasonic beacon transmission further including a first encoded information signal; decoding, by the apparatus and based on the first pilot signal, the first encoded information signal to identify a first medical system associated with the first ultrasonic beacon transmission; entering, by the apparatus, based on the decoding of the first encoded information signal, into a first pairing state in which the apparatus is communicatively paired with the first medical system; detecting, by the apparatus and while operating in the first pairing state and within a threshold time of entering the first pairing state, a second pilot signal included in a second ultrasonic beacon transmission, the second ultrasonic beacon transmission further including a second encoded information signal; and continuing, by the apparatus and based on the detection of the second pilot signal within the threshold time, operating in the first pairing state without decoding the second encoded information signal.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 7 shows an illustrative device pairing system.

DETAILED DESCRIPTION

Beacon-based systems, methods, and apparatuses for managing communicative pairing of an apparatus (or device) with a medical system will be described herein. The systems and methods described herein may be implemented as part of or in conjunction with a medical system, such as a computer-assisted surgical system. As such, an illustrative computer-assisted surgical system will now be described. The following illustrative computer-assisted surgical system is illustrative and not limiting, as the systems and methods described herein may be implemented as part of or in conjunction with other suitable medical systems.

Figure 1:
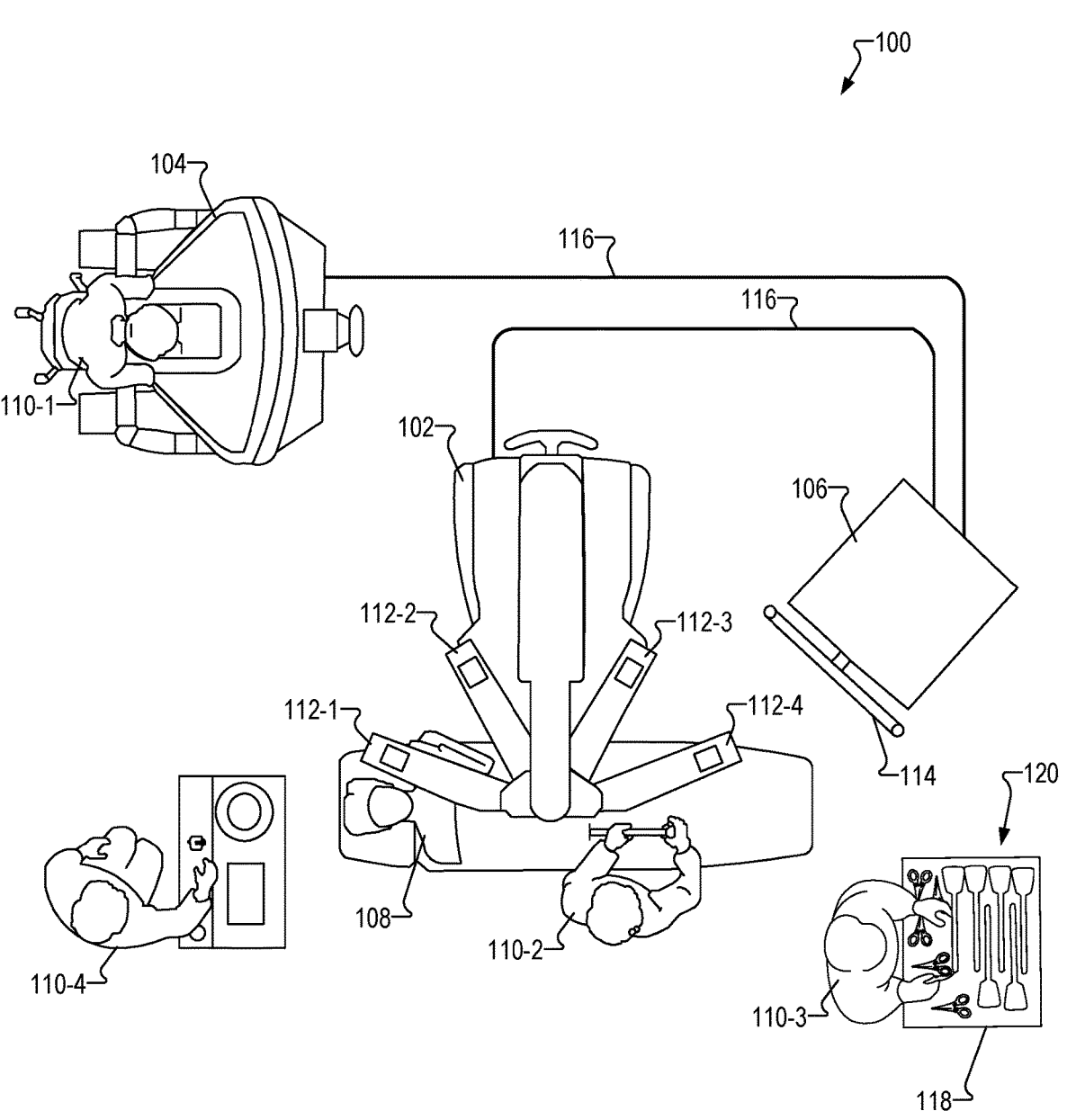
FIG. 1 shows an illustrative computer-assisted surgical system.

FIG. 1 shows an illustrative computer-assisted surgical system 100 ("surgical system 100"). As shown, surgical system 100 may include a manipulating system 102, a user control system 104, and an auxiliary system 106 communicatively coupled one to another. In some examples, surgical system 100 may be implemented by one or more of these components. However, surgical system 100 is not limited to these components, and may include additional components as may suit a particular implementation, such as but not limited to a patient operating table, third-party components (e.g., electrosurgical units) connected to surgical system 100, and the like.

Surgical system 100 may be utilized by a surgical team to perform a computer-assisted surgical procedure on a patient 108. As shown, the surgical team may include a surgeon 110-1, an assistant 110-2, a nurse 110-3, and an anesthesiologist 110-4, all of whom may be collectively referred to as "surgical team members 110." Additional or alternative surgical team members may be present during a surgical session as may serve a particular implementation.

While FIG. 1 illustrates an ongoing minimally invasive surgical procedure, surgical system 100 may similarly be used to perform open surgical procedures or other types of surgical procedures that may similarly benefit from the accuracy and convenience of surgical system 100. Additionally, it will be understood that the surgical session throughout which surgical system 100 may be employed may not only include an operative phase of a surgical procedure, as is illustrated in FIG. 1, but may also include preoperative, postoperative, and/or other suitable phases of the surgical procedure. A surgical procedure may include any procedure in which manual and/or instrumental techniques are used on a patient to investigate, diagnose, and/or treat a physical condition of the patient, Additionally, a surgical procedure may include any non-clinical procedure, e.g., a procedure that is not performed on a live patient, such as a calibration or testing procedure, a training procedure, and an experimental or research procedure.

As shown in FIG. 1, manipulating system 102 may include a plurality of manipulator arms 112 (e.g., manipulator arm 112-1 through 112-4) to which a plurality of surgical instruments (not shown in FIG. 1) may be coupled. Each surgical instrument may be implemented by any suitable therapeutic instrument (e.g., a tool having tissue-interaction functions), imaging device (e.g., an endoscope), diagnostic instrument, or the like that may be used for a computer-assisted surgical procedure (e.g., by being at least partially inserted into patient 108 and manipulated to perform a computer-assisted surgical procedure on patient 108). In some examples, one or more of the surgical instruments may include force-sensing and/or other sensing capabilities. While manipulating system 102 is depicted and described herein as including four manipulator arms 112, it will be recognized that manipulating system 102 may include only a single manipulator arm 112 or any other number of manipulator arms as may serve a particular implementation.

Manipulator arms 112 and/or surgical instruments attached to manipulator arms 112 may include one or more sensors (e.g., displacement transducers, orientational sensors, positional sensors, etc.) used to generate (i.e., uncorrected) kinematics information (hereinafter "surgical system sensors"). Kinematics information may include information such as pose (e.g., position and/or orientation), movement (e.g., velocity, direction, acceleration, etc.), state (e.g., open, closed, stowed, etc.), and/or other attributes of manipulator arms 112, surgical instruments coupled to manipulator arms 112, and/or any other components of manipulating system 102 (e.g., boom arms). One or more components of surgical system 100 may be configured to use the kinematics information to track (e.g., determine poses, movements, and/or states of) and/or control manipulator arms 112 and/or surgical instruments, Manipulating system 102 may also include other sensors configured to generate other information as may suit a particular implementation. Such sensors may also be referred to as "surgical system sensors" and may include, for example, draping sensors, boom height sensors, and the like.

Surgical instruments attached to manipulator arms 112 may each be positioned at a surgical area associated with a patient. A "surgical area" may, in certain examples, be entirely disposed within a patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located In other examples, a surgical area may be at least partially disposed external to the patient at or near where a surgical procedure is planned to be performed, is being performed, or has been performed on the patient. For instance, surgical system 100 may be used to perform an open surgical procedure such that part of the surgical area (e.g., tissue being operated on) is internal to the patient while another part of the surgical area (e.g., a space around the tissue where one or more surgical instruments may be disposed) is external to the patient. A surgical instrument may be referred to as being positioned or located at or within a surgical area when at least a portion of the surgical instrument (e.g., a distal portion of the surgical instrument) is located within the surgical area.

User control system 104 may be configured to facilitate control by surgeon 110-1 of surgical system 100 (e.g., manipulator arms 112 and surgical instruments attached to manipulator arms 112). For example, surgeon 110-1 may interact with user input devices included in user control system 104 to remotely move or manipulate manipulator arms 112 and the surgical instruments coupled to manipulator arms 112. To this end, user control system 104 may provide surgeon 110-1 with imagery (e.g., high-definition stereoscopic imagery) of a surgical area associated with patient 108 as captured by an imaging device (e.g., a stereoscopic endoscope). Surgeon 110-1 may utilize the imagery to perform one or more procedures with one or more surgical instruments coupled to manipulator arms 112.

To facilitate control of surgical instruments, user control system 104 may include a set of master controls (not shown in FIG. 1). These master controls may be manipulated by surgeon 110-1 to control movement of surgical instruments (e.g., by utilizing robotic and/or teleoperation technology). The master controls may be configured to detect a wide variety of hand, wrist, and finger movements by surgeon 110-1. In this manner, surgeon 110-1 may intuitively perform a surgical procedure using one or more surgical instruments.

User control system 104 may further be configured to facilitate control by surgeon 110-1 of other components of surgical system 100. For example, surgeon 110-1 may interact with user control system 104 to change a configuration or operating mode of surgical system 100, to change a display mode of surgical system 100, to generate additional control signals used to control surgical instruments attached to manipulator arms 112, to facilitate switching control from one surgical instrument to another, or to perform any other suitable operation. To this end, user control system 104 may also include one or more additional user input devices (e.g., foot pedals, buttons, switches, touchscreen displays, etc.) configured to receive manual input from surgeon 110-1. In some examples, user control system 104 may also include one or more audio input devices (e.g., microphones) configured to receive audio input (e.g., voice input) from one or more users, and one or more audio output devices (e.g., speakers).

Auxiliary system 106 may include one or more computing devices configured to perform primary processing operations of surgical system 100. The one or more computing devices included in auxiliary system 106 may control and/or coordinate operations performed by various other components (e.g., manipulating system 102 and/or user control system 104) of surgical system 100. For example, a computing device included in user control system 104 may transmit instructions to manipulating system 102 by way of the one or more computing devices included in auxiliary system 106. As another example, auxiliary system 106 may receive from manipulating system 102 (e.g., from an imaging device) and process image data representative of imagery captured by an endoscope attached to a manipulator arm 112.

In some examples, auxiliary system 106 may be configured to present visual content to surgical team members 110 who may not have access to the imagery provided to surgeon 110-1 at user control system 104. To this end, auxiliary system 106 may include a display monitor 114 configured to display one or more user interfaces, such as images (e.g., 2D images) of the surgical area, information associated with patient 108 and/or the surgical procedure, and/or any other visual content as may serve a particular implementation. For example, display monitor 114 may display images of the surgical area together with additional content (e.g., graphical content, contextual information, etc.) concurrently displayed with the images. In some embodiments, display monitor 114 is implemented by a touchscreen display with which surgical team members 110 may interact (e.g., by way of touch gestures) to provide user input to surgical system 100.

While auxiliary system 106 is shown in FIG. 1 as a separate system from manipulating system 102 and user control system 104, auxiliary system 106 may be included in, or may be distributed across, manipulating system 102 and/or user control system 104. Additionally, while user control system 104 has been described as including one or more user input devices and/or audio input devices, other components of surgical system 100 (e.g., manipulating system 102 and/or auxiliary system 106) may include user input devices, audio input devices, and/or audio output devices as may suit a particular implementation.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any optical, wired, or wireless communication link as may serve a particular implementation. To this end, manipulating system 102, user control system 104, and auxiliary system 106 may each include one or more optical, wired, or wireless communication interfaces, such as one or more local area network interfaces, Wi-Fi network interfaces, cellular interfaces, etc.

As shown in FIG. 1, surgical system 100 may also include an accessory cart 118. Accessory cart 118 may be configured to carry or store certain accessories of surgical system 100 and/or supplies to be used during the surgical procedure. For example, accessory cart 118 may hold surgical instruments 120 that may be coupled with manipulator arms 112 as needed during the surgical procedure.

In alternative embodiments, accessory cart 118 is not included in surgical system 100 but is a standalone medical system. For example, accessory cart 118 may be used to deliver sterilized instruments from a sterile processing department ("SPD") of a hospital to various operating rooms throughout the hospital. Thus, in these embodiments accessory cart 118 is not included in surgical system 100 but may be a separate medical system.

In some examples, a medical system (e.g., surgical system 100, accessory cart 118, etc.) may be located within a medical facility that uses one or more ultrasonic beacons to facilitate communicative pairing of one or more devices with the medical system and/or to provide contextual information about the medical system, such as information about a medical procedure performed with the medical system, the location of the medical system, errors of the medical system, and the like.

Figure 2:
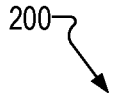
FIG. 2 shows an illustrative configuration of a medical facility including a beacon generator and a medical system located within a predefined area.
Figure 2:
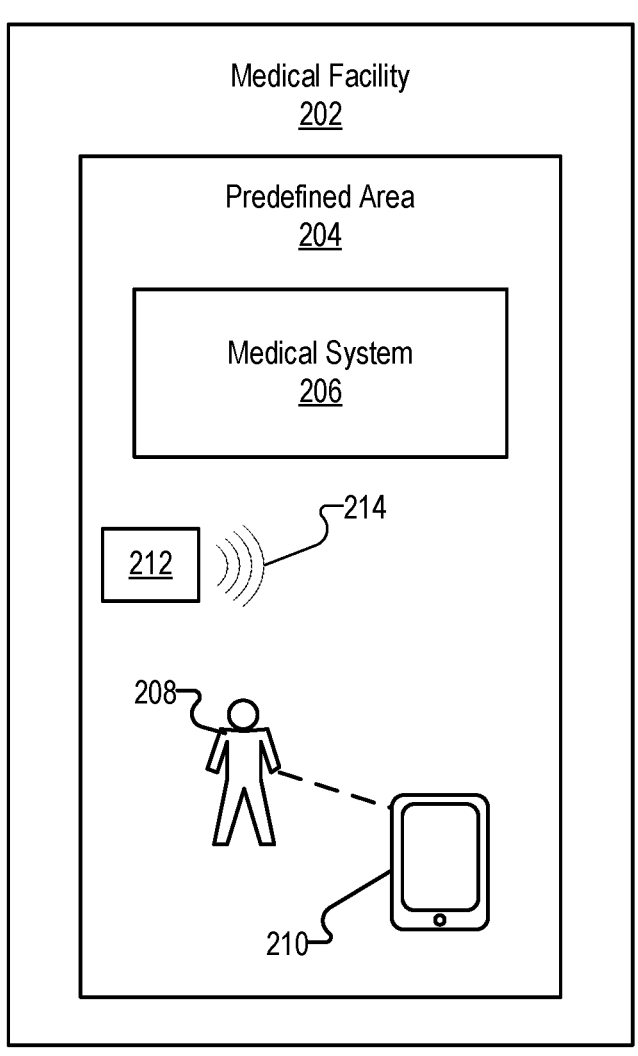

FIG. 2 shows an illustrative configuration 200 of a medical facility 202. As shown, medical facility 202 includes a predefined area 204 and a medical system 206 located within predefined area 204. Medical facility 202 may be, for example, a hospital, a unit within a hospital (e.g., an emergency room, a trauma center, a maternity unit, an intensive care unit, etc.), a surgical facility, a deployable field hospital, a medical clinic, a doctor's office, a dentist's office, a nursing home, a hospice facility, a rehab facility, an assisted living facility, or any other similar facility. Predefined area 204 may be a particular area (e.g., a particular room) within medical facility 202 in which medical system 206 is located and/or used to perform one or more tasks or operations with respect to a patient. For example, predefined area 204 may be an operating room, a recovery room, a consulting room, a patient room, an examination room, an equipment room, and the like. In some examples, predefined area 204 is defined by and/or separated from other areas of medical facility 202 (e.g., from an adjoining operating room, from a hallway, from an equipment room, etc.) by one or more physical barriers (e.g., walls, windows, doors, curtains, etc.).

Medical system 206 may be implemented by any type of medical system that may be used to monitor, treat, and/or assist a patient located within medical facility 202. For example, medical system 206 may be implemented by a surgical system (e.g., a computer-assisted surgical system, such as surgical system 100), an imaging system (e.g., a computed tomography (CT) scanner, a magnetic resonance imaging (MRI) scanner, an X-ray machine, etc.), a dialysis machine, a heart—lung machine, a monitoring device (e.g., a heartrate monitor, a blood pressure monitor, etc.), a ventilator, a patient bed, an accessory cart, and/or the like. In some examples, medical system 206 is implemented by a mobile accessory cart (e.g., accessory cart 118) that may move throughout medical facility 202. For example, a mobile accessory cart may be an SPD cart that may be used to deliver sterilized instruments throughout medical facility 202 (e.g., to distribute sterilized instruments to various operating rooms).

A user 208 and a user device 210 associated with user 208 (e.g., used by, carried by, operated by, and/or logged into by user 208) may move throughout medical facility 202. As shown in FIG. 2, user 208 and user device 210 are physically located within predefined area 204. User device 210 is representative of any type of device (also referred to herein as an "apparatus") that may communicate, directly or indirectly, with medical system 206, such as an auxiliary device, a component of medical system 206 (e.g., manipulating system 102, user control system 104, auxiliary system 106, etc.), an accessory cart, and any other suitable device. An auxiliary device may include any device that is not part of medical system 206, such as a user device, another medical device or medical system, an SPD cart, and/or any other suitable device. A user device (e.g., user device 210) may be any device capable of presenting information to a user, whether in visual, audio, or haptic format, and/or receiving user input from the user. For example, a user device may be implemented by a mobile device (e.g., a mobile phone, a handheld device, a tablet computing device, a laptop computer, a personal computer, etc.), an audio device (e.g., a speaker, earphones, etc.), a wearable device (e.g., a smartwatch device, an activity tracker, a head-mounted display device, a virtual or augmented reality device, etc.), and/or a display device (e.g., a television, a projector, a monitor, a touch screen display device, etc.).

Medical system 206 may be configured to communicatively pair with user device 210 when user device 210 is in proximity to medical system 206. For example, as shown in FIG. 2, user 208 (e.g., a surgical team member 110) located within medical facility 202 may gain access, by way of user device 210, to one or more functional features (e.g., an endoscopic video feed, a settings menu, medical system controls, etc.) associated with medical system 206 when user device 210 is communicatively paired with medical system 206. For instance, user 208 may, by way of an application executed by user device 210, view content associated with medical system 206, interact with medical system 206, and/or communicate with other users via additional user devices that are communicatively paired with medical system 206. Even when user device 210 is not communicatively paired with medical system 206, user 208 may have access to other functional features associated with medical facility 202. For example, user 208 may, by way of an application executed by user device 210, view and/or edit medical personnel information, update user profile information, view training content, schedule tasks, schedule medical procedures, view patient information, and the like.

To facilitate communicative pairing of user device 210 with medical system 206, a beacon generator 212 (e.g., an ultrasonic transducer) is located within predefined area 204 and configured to generate and emit an ultrasonic beacon

214 that is associated with medical system 206. Ultrasonic beacon 214 comprises sound waves generally having a frequency above the human audible hearing range (e.g., above about 17 kHz or above 20 kHz) In some examples, ultrasonic beacon 214 has a frequency between about 17 kHz and about 20 kHz.

Ultrasonic beacon 214 may include repeated transmissions of a particular message. For each transmission of ultrasonic beacon 214, beacon generator 212 may include (e.g., encode) the message in ultrasonic beacon 214 by modulating one or more of the amplitude, frequency, and waveform of ultrasonic signals, such as by using phase-shift keying (PSK), binary phase-shift keying (BPSK), quadrature phase-shift keying (QPSK), amplitude-shift keying (ASK), frequency shift keying (FSK), on-off keying (OOK), quadrature amplitude modulation (QAM), an audio OR code format, by multi-frequency bit-coding, or any other suitable modulation technique.

The message included (e.g., encoded) in ultrasonic beacon 214 may include information (e.g., contextual information and/or identification information) associated with medical system 206. In some examples, the message information encoded in ultrasonic beacon 214 associates, or may be used to associate, ultrasonic beacon 214 with medical system 206. For example, ultrasonic beacon 214 may include a location identifier that identifies the predefined area (i.e., predefined area 204) in which ultrasonic beacon 214 is located. The location identifier may be, for example, a unique identification ("ID") number (e.g., a room number) assigned to or otherwise representative of predefined area 204. As another example, ultrasonic beacon 214 may include a medical system identifier (e.g., a surgical system identifier) that identifies the medical system (i.e., medical system 206) with which ultrasonic beacon 214 is associated. The medical system identifier may be, for example, a unique medical system ID assigned to or otherwise representative of medical system 206. Additionally or alternatively, the medical system identifier may be a network address for the medical system. As yet another example, ultrasonic beacon 214 may include a beacon generator identifier that identifies the particular beacon generator (i.e., beacon generator 212) that emits ultrasonic beacon 214. The beacon generator identifier may be a beacon generator ID assigned to or otherwise representative of beacon generator 212. As a further example, ultrasonic beacon 214 may include a medical session identifier that identifies a particular medical session with which ultrasonic beacon 214 is associated. The medical session identifier may be a medical session ID assigned to or otherwise representative of a particular medical session (e.g., a patient ID, medical team personnel IDs, a surgeon ID, a room ID, a surgical session ID, etc.). In some examples, the identification information may comprise a combination of letters and numbers (e.g., a 10-digit number). It will be recognized that the foregoing information that may be included in ultrasonic beacon 214 is merely illustrative and not limiting, as ultrasonic beacon 214 may include any other suitable information (e.g., GPS coordinates, error information, status information, security information, authentication information, etc.).

Each transmission of ultrasonic beacon 214 may include an information signal in which the message is encoded and a pilot signal, which may be used for synchronization of transmissions of ultrasonic beacon 214 and decoding the encoded message. The pilot signal may also help characterize the transmission and may carry some preamble information that may be used in decoding the information signal. In some examples, such as when the information included in ultrasonic beacon 214 has a small bit size, ultrasonic beacon 214 is transmitted over a single channel (e.g., in a single carrier communication scheme), In other examples, such as when the information included in ultrasonic beacon 214 has a relatively large bit-size (e.g., 32 bits, 64 bits, etc.), ultrasonic beacon 214 may be transmitted over multiple subchannels in a multi-carrier communication scheme (e.g., frequency division multiplexing (FDM) or orthogonal frequency division multiplexing modulation (OFDM)).

Figure 3:
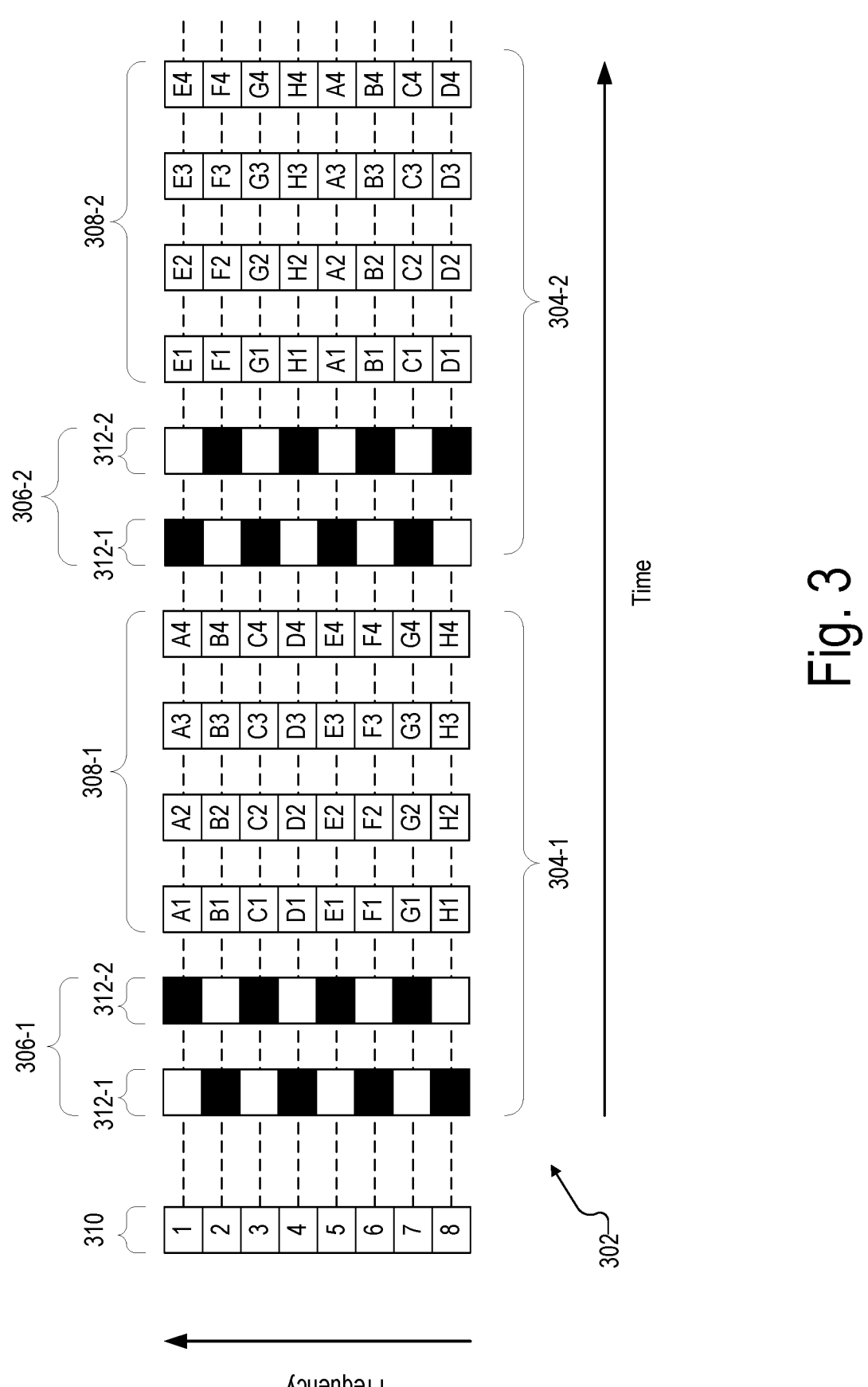
FIG. 3 shows an illustrative configuration of ultrasonic beacon transmissions of an ultrasonic beacon.

FIG. 3 shows an illustrative configuration 300 of a communication scheme for an ultrasonic beacon 302 ("beacon 302"). While FIG. 3 shows a multi-channel communication scheme, in other embodiments the communication scheme may be a single-channel communication scheme. FIG. 3 shows a first transmission 304-1 of beacon 302 and a second transmission 304-2 of beacon 302. Second transmission 304-2 is subsequent to first transmission 304-1. For ease of discussion FIG. 3 shows two transmissions, but beacon 302 may have any other suitable number of transmissions. Transmissions 304 may be repeated continuously until beacon 302 is terminated (e.g., beacon generator 212 is turned off). For example, a third transmission identical to first transmission 304-1 may follow second transmission 304-2, a fourth transmission identical to second transmission 304-2 may follow the third transmission, and so on. Beacon 302 may be transmitted with any suitable frequency (e.g., time between successive pilot signals 306), such as 100 Hz, 10 Hz, 1 Hz, etc.

Transmissions 304-1 and 304-2 of beacon 302 include a pilot signal 306-1 and a pilot signal 306-2, respectively, and an information signal 308-1 and an information signal 308-2, respectively. Pilot signals 306 and information signals 308 are transmitted on a plurality of subchannels 310 (e.g., subchannels 310-1 to 310-8). For ease of discussion FIG. 3 shows that beacon 302 is transmitted on eight different subchannels 310, but beacon 302 may be transmitted on any other number of subchannels as may serve a particular implementation (e.g., 2, 4, 10, 3, 20, 32, 64, etc.) or on a single channel in a single-channel communication scheme. Subchannels 310 may be within the ultrasonic range. In some examples, the bandwidth of the plurality of subchannels 310 is within about 17.5 kHz to about 20 kHz. However, the plurality of subchannels 310 may have any other suitable range as may serve a particular implementation.

In some examples, pilot signals 306 and information signals 308 are encoded in accordance with OOK. Accordingly, each bit is represented by the transmission of a particular frequency for a set period of time or the absence of transmission of a particular frequency for a set period of time. In alternative examples, pilot signals 306 and information signals 308 may be encoded with any other suitable encoding scheme, such as PSK, FSK, OAR etc.

Pilot signals 306 are configured to provide information for synchronization of transmissions 304. Pilot signals 306 may also contain other information that may be used for decoding information signals 308. As shown in FIG. 3, each pilot signal 306 includes a first set of signals 312-1 ("first set 312-1") transmitted on subchannels 310 followed by a second set of signals 312-2 ('second set 312-2") transmitted on subchannels 310. Second set 312-2 is the inverse of first set 312-1 (e.g., a subchannel that transmits an ON signal (represented by a white box) in first set 312-1 transmits an OFF signal (represented by a black box) in second set 312-2, and vice versa). As a result, the switch from first set 312-1 to second set 312-2 produces a strong edge that is easily detectable. This sharp edge, when detected by a device (e.g., user device 210), indicates the start of each transmission 304 and thus facilitates synchronization of transmissions 304. While pilot signals 306 are shown and described as having two sets 312 of signals, pilot signals 306 may have more or fewer sets of signals. In some examples, each pilot signal 306 may comprise a more compact signal for providing synchronization information and any other desired information.

First set 312-1 and second set 312-2 may have any suitable signal pattern as may serve a particular implementation. As shown in FIG. 3, first set 312-1 and second set 312-2 each comprise an alternating pattern of ON/OFF signals. However, sets 312 are not limited to this configuration, and may have any other suitable configurations. In some examples, first set 312-1 and second set 312-2 may have a unique pattern configured to convey other information, such as a permutation order, as will be explained below in more detail.

Information signals 308 are configured to transmit message information such as identification information. In some examples, the message information encoded in information signals 308 may be divided into multiple subparts, and each subpart may include one or more bits. For ease of discussion, FIG. 3 shows that each information signal 308 is divided into eight message subparts denoted A through H, and each message subpart is transmitted in a single subchannel in four successive ON or OFF signals. For example, message subpart A of first transmission 304-1 is transmitted on subchannel 310-1 as signal A1, followed by signal A2, followed by signal A3, followed by signal A4. Message subparts B through H are transmitted on subchannels 310-2 to 310-8, respectively, in a similar manner. It will be recognized that each information signal 308 may be divided into any suitable number of subparts (e.g., 2, 4, 10, 3, 20, 32, 64, etc.), and each message subpart may be transmitted as any one or more number of signals as may serve a particular implementation.

In some examples, the beacon generator permutes the message subparts that are transmitted on subchannels 310 for each successive transmission 304 of beacon 302. The beacon generator may permute the message subparts in any suitable way. In some examples, the message subparts are shifted on subchannels 310 by one-half (½) of the total bandwidth of the spectrum of subchannels 310. For example, as shown in FIG. 3 message subpart A is transmitted on subchannel 310-1 in first transmission 304-1 and is shifted to subchannel 310-5 in second transmission 304-2. Similarly, message subparts B, G. and D are shifted from subchannels 2, 3, and 4 in first transmission 304-1 to subchannels 6, 7, and 8 in second transmission 304-2, respectively. Message subparts E to H are shifted from subchannels 5 to 8 in first transmission 304-1 to subchannels 1-4 in second transmission 304-2, respectively. First and second transmissions 304 may then be repeated indefinitely or until terminated.

When a device (e.g., user device 210) detects first transmission 304-1 (e.g., detects pilot signal 306-1), the device uses pilot signal 306-1 to decode information signal 308-1 by assembling each message subpart (e.g., signals A1 to A4), and then assembling message subparts A to H to reconstruct the complete message information. In this way, the multichannel communication scheme shown in FIG. 3 may transmit, by beacon 302, multi-digit information (e.g., a 10-digit number represented by 32 bits, a 6-digit number represented by 20 bits, etc.) and/or any other suitable information in a relatively short amount of time. Systems and methods for using pilot signals in transmitting and decoding ultrasonic beacons are described in more detail in International Patent Application No. PCT/US2020/62065 filed Nov. 24, 2020, which application is incorporated herein by reference in its entirety.

While FIG. 3 shows that transmissions 304 of beacon 302 include pilot signals 306 directly preceding information signals 308 in the same channels, transmissions 304 are not limited to this configuration. In other configurations, transmissions 304 may include pilot signals 306 and information signals 308 transmitted on different channels. In some examples, the pilot signals 308 and information signals 308 may be transmitted simultaneously or alternatingly in a predetermined pattern.

Referring again to FIG. 2, user device 210 may detect ultrasonic beacon 214 (or beacon 302) in any suitable way. For example, user device 210 may include an ultrasonic sensor (e.g., a microphone) configured to detect ambient sound waves, including ultrasonic beacon 214 or beacon 302, and process the detected ambient sound waves to generate audio signals representative of the detected ambient sound waves. In some examples, an application executed by user device 210 may process the audio signals to filter out audio signals that do not meet a predefined set of criteria (e.g., audio signals that are not in the ultrasonic range, do not fall within a predefined amplitude range, etc.). The ultrasonic sensor may also be set, either automatically by the application or manually by a user, to an "always-on" state. In this way, user device 210 may continually monitor for ultrasonic beacon transmissions while user device 210 is located within medical facility.

User device 210 is configured to detect (e.g., via an ultrasonic sensor, such as a microphone, etc.) ultrasonic beacon 214 when user device 210 is in proximity to beacon generator 212. In some examples, ultrasonic beacon 214 is configured to not transmit through solid barriers (e.g., walls) and/or is configured to be confined within predefined area 204. Accordingly, user device 210 may detect ultrasonic beacon 214 only when user device 210 is located within the same predefined area (e.g., operating room) as beacon generator 212, as shown in FIG. 2, When user device 210 is not located within predefined area 204, user device 210 does not detect ultrasonic beacon 214. Examples of user device 210 detecting ultrasonic beacon 214 will be described below in more detail.

As shown in FIG. 2, beacon generator 212 is a standalone device separate from medical system 206 (e.g., beacon generator 212 is not physically integrated with or controlled by medical system 206). As a standalone device beacon generator 212 may be fixedly positioned at any suitable location within predefined area 204, such as on a wall or ceiling of predefined area 204. Alternatively, beacon generator 212 may be a movable standalone device that may be moved and positioned as desired within predefined area 204 and/or within medical facility 202.

Figure 4:
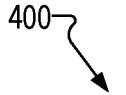
FIGS. 4-7 show various alternative illustrative configurations of a medical facility including one or more beacon generators and one or more medical systems.
Figure 4:
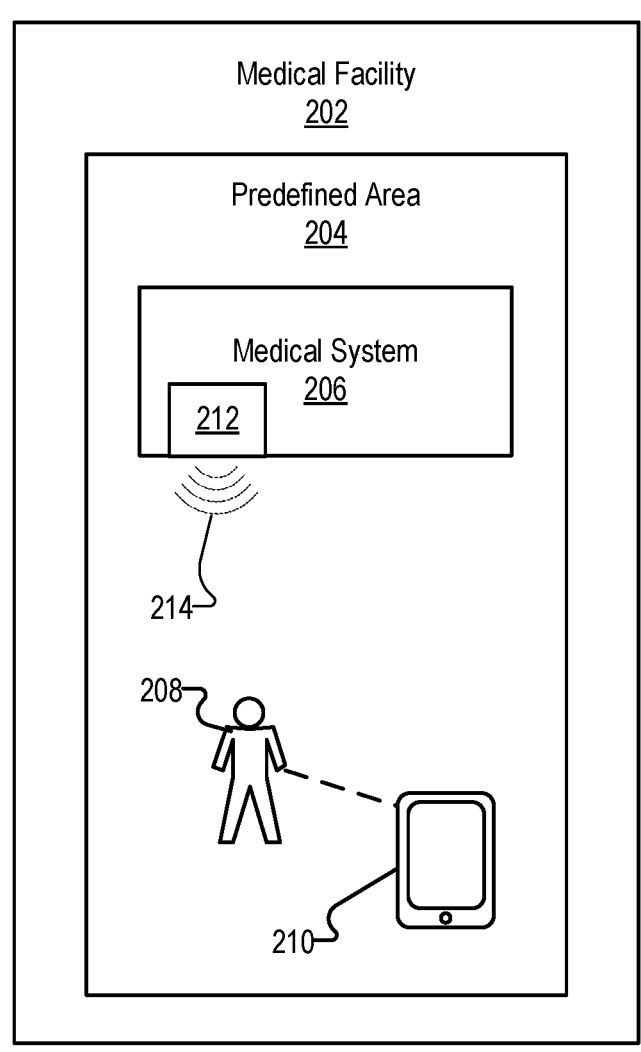

Alternatively to a standalone device separate from medical system 206, beacon generator 212 may be included in medical system 206, as shown in FIG. 4. FIG. 4 shows another illustrative configuration 400 of medical facility 202. FIG. 4 is similar to FIG. 2 except that in FIG. 4 beacon generator 212 is included in medical system 206. Beacon generator 212 may be included in medical system 206 in any suitable way. For example, beacon generator 212 may be physically integrated with medical system 206 (e.g., mounted on a column of manipulating system 102, included in user control system 104, etc.). Thus, if medical system 206 is moved to a different area of medical facility 202, beacon generator 212 also moves to the new area. Additionally or alternatively, beacon generator 212 may be controlled by medical system 206. For example, medical system 206 (e.g., auxiliary system 106 of surgical system 100) may configure ultrasonic beacon 214 to include information and may control the emission of ultrasonic beacon 214 by beacon generator 212.

Figure 5:
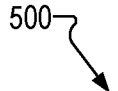
Figure 5:
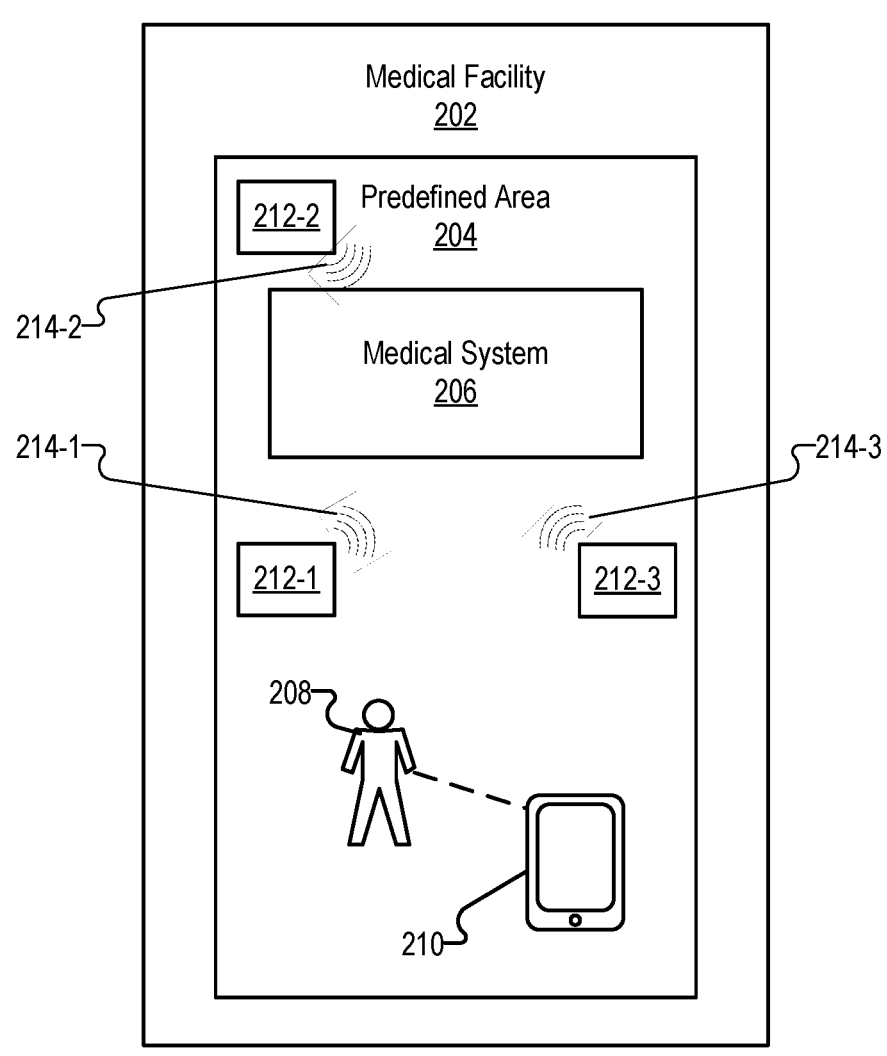

The illustrative configurations 200 and 400 of medical facility 202 described above include a single beacon generator 212 located within predefined area 204. However, multiple beacon generators 212 may be located within predefined area 204, as illustrated in FIG. 5. FIG. 5 shows another illustrative configuration 500 of medical facility 202. FIG. 5 is similar to FIG. 2 except that in FIG. 5 predefined area 204 includes three beacon generators 212 (e.g., beacon generators 212-1 through 212-3) configured to emit ultrasonic beacons 214 (e.g., ultrasonic beacons 214-1 through 214-3) associated with medical system 206. It will be recognized, however, that predefined area 204 may include any other number of beacon generators 212 as may suit a particular implementation.

Ultrasonic beacons 214 may each include information (e.g., information encoded in an information signal of ultrasonic beacon 214) that may be used by a device pairing system to identify a particular medical system (i.e., medical system 206) that is associated with ultrasonic beacons 214 and/or to control communicative pairing of user device 210 with medical system 206. In some examples, ultrasonic beacons 214 each include the same information (e.g., the same location ID). In additional or alternative examples, each ultrasonic beacon 214 includes unique identification information. For example, ultrasonic beacon 214-1 may include a surgical system identifier, ultrasonic beacon 214-2 may include a location identifier, and ultrasonic beacon 214-3 may include a patient identifier. In some examples, one or more beacon generators 212 (or components or devices connected to or associated with beacon generators 212) may be configured to listen for and detect ultrasonic beacons 214 emitted by the other beacon generators 212 located within predefined area 204 and use the detected ultrasonic beacons 214 to coordinate transmission of ultrasonic beacons 214 so as to avoid or minimize interference.

Figure 6:
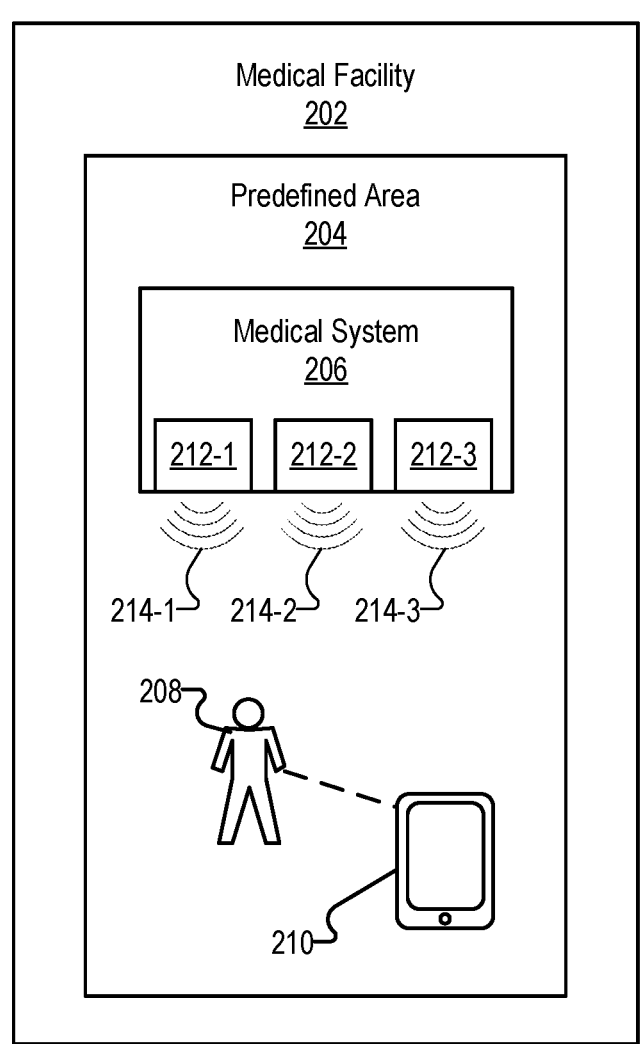

In some examples, multiple beacon generators 212 may be included in medical system 206, as shown in FIG. 6. FIG. 6 shows another illustrative configuration 600 of medical facility 202. FIG. 6 is similar to FIG. 5 except that beacon generators 212 (e.g., beacon generators 212-1 through 212-3) are included in medical system 206. Beacon generators 212 may be included in medical system 206 in any suitable way. For example, beacon generators 212 may be physically integrated with and/or controlled by medical system 206, as explained above. In some examples, each beacon generator 212 is included in a different component of medical system 206. For instance, if medical system 206 is implemented by surgical system 100, beacon generator 212-1 may be included in manipulating system 102, beacon generator 212-2 may be included in user control system 104, and beacon generator 212-3 may be included in auxiliary system 106.

In some examples, ultrasonic beacons 214 include the same information (e.g., the same medical system ID). In additional or alternative examples, each ultrasonic beacon 214 includes unique information. For example, when medical system 206 includes multiple components, various components may each include a beacon generator 212 and each ultrasonic beacon 214 may include a unique component identifier (e.g., a component ID) assigned to or otherwise representative of the particular component in which the beacon generator 212 is included. For instance, referring again to the example in which medical system 206 is implemented by surgical system 100, ultrasonic beacon 214-1 may include a unique component ID for manipulating system 102, ultrasonic beacon 214-2 may include a unique component ID for user control system 104, and ultrasonic beacon 214-3 may include a unique component ID for auxiliary system 106.

Figure 7:
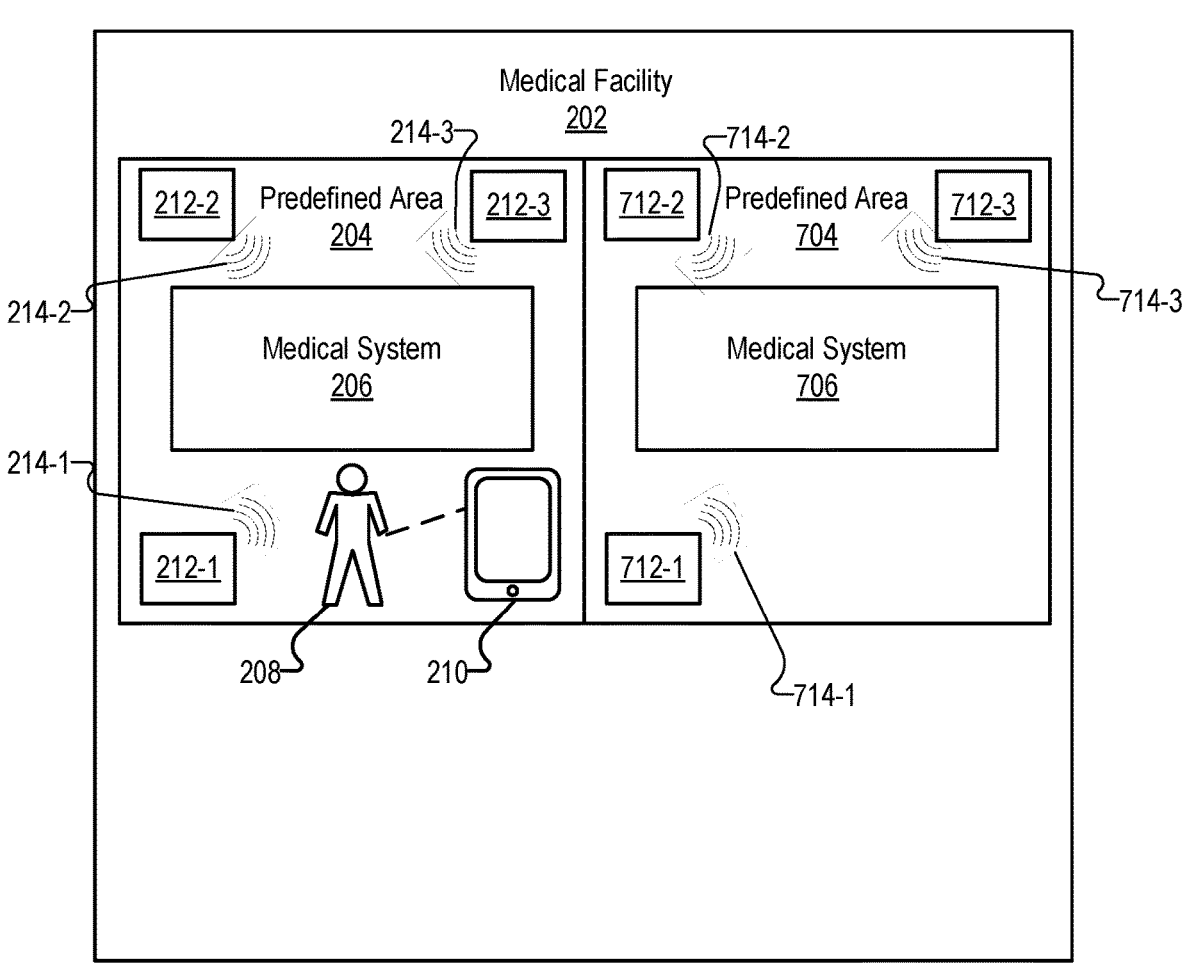

In some configurations, medical facility 202 may also include additional beacon generators (not shown in FIGS. 5 and 6) in areas outside of predefined area 204, as illustrated in FIG. 7. FIG. 7 shows another illustrative configuration 700 of medical facility 202. FIG. 7 is similar to FIG. 5 except that in FIG. 7 medical facility 202 includes an additional predefined area 704 (e.g., another operating room, a hallway, an equipment room, etc.) adjoining predefined area 204, an additional medical system 706 located in predefined area 704, and additional beacon generators 712 (e.g., beacon generators 712-1 through 712-3) located within predefined area 704 and that emit ultrasonic beacons 714 (e.g., ultrasonic beacons 714-1 through 714-3) associated with additional medical system 706, It will be recognized that any of beacon generators 212-1 through 212-3 may alternatively be included in medical system 206, and any of beacon generators 712-1 through 712-3 may alternatively be included in medical system 702, in the manner described above with reference to FIG. 5. Additionally, predefined areas 204 and 704 may each include any other number of beacon generators 212 and 712, respectively, as may suit a particular implementation. In some examples, predefined area 704 does not include a medical system but may nevertheless include one or more beacon generators 712. For example, predefined area 704 may be a hallway, a break room, an office, or any other location.

It will be recognized that the foregoing configurations of medical facility 202 are merely illustrative and not limiting, as medical facility 202 may include any number and configuration of predefined areas, medical systems, and beacon generators as may suit a particular implementation. Moreover, any of the configurations described herein may be modified or combined as may suit a particular implementation.

Figure 8:
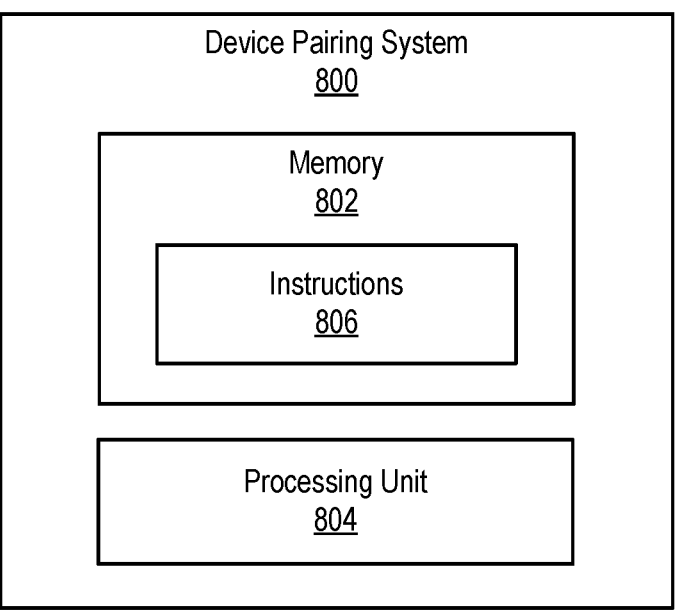

As mentioned, ultrasonic beacons 214 may include information that may be used by a device pairing system to facilitate and/or manage communicative pairing of a device (e.g., user device 210) with a medical system (e.g., medical system 206). FIG. 8 shows an illustrative device pairing system 800 ("pairing system 800") that may be configured to communicatively pair a device with a medical system and manage (e.g., control, configure, change, set parameters for, etc.) a pairing state of the device. Pairing system 800 may be included in, implemented by, or connected to any medical systems, devices, or other computing systems described herein. For example, pairing system 800 may be implemented by a computer-assisted surgical system (e.g., surgical system 100). As another example, pairing system 800 may be implemented by a stand-alone computing system communicatively coupled to a medical system. In some examples, pairing system 800 may be implemented, in whole or in part, by a device (e.g., user device 210).

As shown in FIG. 8, pairing system 800 includes, without limitation, a memory 802 and a processing unit 804 selectively and communicatively coupled to one another. Memory 802 and processing unit 804 may each include or be implemented by hardware and/or software components (e.g., processors, memories, communication interfaces, instructions stored in memory for execution by the processors, etc.). For example, memory 802 and processing unit 804 may be implemented by any component in a medical system. In some examples, memory 802 and processing unit 804 may be distributed between multiple devices and/or multiple locations as may serve a particular implementation.

Memory 802 may maintain (e.g., store) executable data used by processing unit 804 to perform any of the operations described herein. For example, memory 802 may store instructions 806 that may be executed by processing unit 804 to perform any of the operations described herein. Instructions 806 may be implemented by any suitable application, software, code, and/or other executable data instance. Memory 802 may also maintain any data received, generated, managed, used, and/or transmitted by processing unit 804.

Processing unit 804 may be configured to perform (e.g., execute instructions 806 stored in memory 802 to perform) various operations associated with pairing a device with a medical system and managing a pairing state of the device with respect to the medical system and/or additional medical systems. Operations that may be performed by processing unit 804 are described herein. In the description that follows, any references to operations performed by pairing system 800 may be understood to be performed by processing unit 804 of pairing system 800.

As mentioned, pairing system 800 may be implemented entirely by the medical system itself. For example, pairing system 800 may be implemented by one or more computing devices included in medical system 206 (e.g., in one or more computing devices included within manipulating system 102, user control system 104, and/or auxiliary system 106 of surgical system 100).

Figure 9:
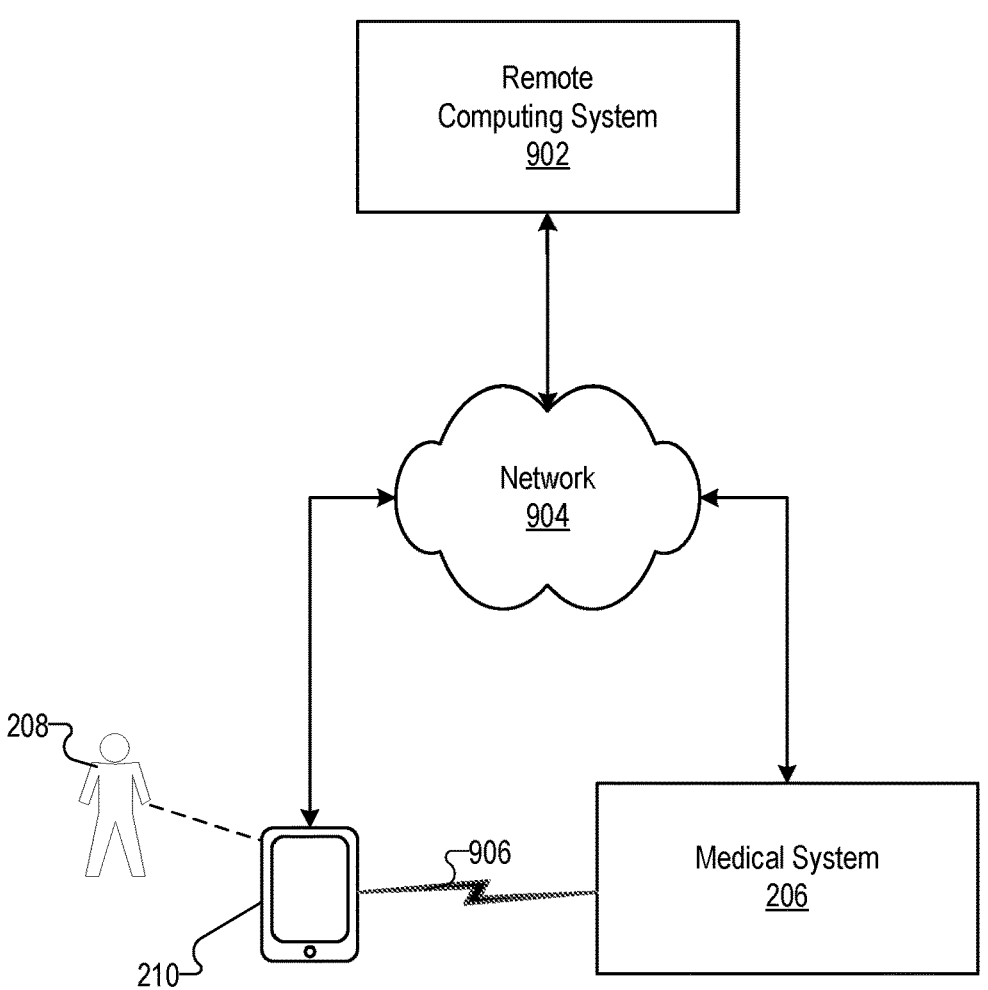
FIG. 9 shows an illustrative implementation of the device pairing system of FIG. 8.

FIG. 9 shows another illustrative implementation 900 of pairing system 800. In implementation 900, a remote computing system 902 may be communicatively coupled to medical system 206 by way of a network 904. Remote computing system 902 may include one or more computing devices (e.g., servers) configured to perform any of the operations described herein. Network 904 may be a local area network, a wireless network (e.g., Wi-Fi), a wide area network, the Internet, a cellular data network, and/or any other suitable network. Data may flow between components connected to network 904 using any communication technologies, devices, media, and protocols as may serve a particular implementation. As shown, user device 210 may be connected to network 904 and thereby communicate with remote computing system 902.

In some examples, remote computing system 902 and/or network 904 are located partly or entirely within a medical facility (e.g., medical facility 202) as part of a medical facility management system (not shown). A medical facility management system may include one or more computing systems configured to generate and/or maintain medical facility data associated with the medical facility and its operations, such as data representative of medical systems included in the medical facility and locations of the medical systems, patient information, beacon generator information and locations of the beacon generators, medical session information, medical personnel information, schedule information, and the like.

In some examples, pairing system 800 is entirely implemented by remote computing system 902 or user device 210. In alternative examples, pairing system 800 is distributed across any two or more of remote computing system 902, medical system 206, and user device 210.

Pairing system 800 is configured to manage a pairing state of user device 210 with respect to one or more medical systems. A "pairing state" of user device 210 may include, without limitation, a "paired state," a "limited paired state," and an "unpaired state," as will now be described.

While operating in a "paired state," user device 210 is communicatively paired with medical system 206 and configured to exchange data with medical system 206, thereby enabling user 208 to access, by way of user device 210, one or more functional features associated with medical system 206. For example, the user may, by way of the device, view content (e.g., an endoscopic video stream, patient information, surgical team information, etc.) associated with the medical system, interact with the medical system (e.g., control one or more features or settings of the medical system), view information (e.g., patient information, surgical team information, etc.) about a medical procedure being performed with the medical system (e.g., a surgical session performed with surgical system 100), and/or communicate with other users by way of additional user devices that are communicatively paired with the medical system. As another example, a user control system for a proctor surgeon may, upon successful pairing with manipulating system 102, be configured to control and interact with a manipulating system 102 that is primarily controlled by a primary user control system 104.

User device 210 may be communicatively paired with medical system 206 in any suitable way. For example, user device 210 may be communicatively paired with medical system 206 by way of an indirect communication link (e.g., by way of remote computing system 902 and/or network 904). Alternatively, user device 210 may be communicatively paired with medical system 206 by way of a direct (e.g., peer-to-peer, single hop, or ad hoc) communication link 906. The direct communication link may include, for example, a direct wireless connection, such as a Bluetooth connection, a near field communication connection, a Wi-Fi connection, a Wi-Fi Direct connection, a smartphone ad hoc network (SPAN) connection, a mobile device ad hoc network (MANET) connection, etc. In some examples, user device 210 may be communicatively paired with medical system 206 only when user device 210 is physically proximate to medical system 206, such as when user device 210 detects an ultrasonic beacon associated with medical system 206 (e.g., ultrasonic beacon 214). It will be recognized, however, that in some examples, user device 210 is not communicatively paired with medical system 206. Communicative pairing of user device 210 with medical system 206 will be described below in more detail.

In an "unpaired" or "not paired" state, user device 210 is not communicatively paired with medical system 206, is not configured to exchange data with medical system 206, and/or does not enable user 208 to access, by way of user device 210, any functional features associated with medical system 206.

User device 210 may also operate in one or more other intermediate pairing states, such as a "limited paired state." In a limited paired state, one or more functional features provided by the device are different (e.g., modified, prohibited, locked, temporarily suspended, conditioned, etc.) than when user device 210 is operating in a paired state. For instance, a proctor surgeon may be able to control operations of surgical system 100 by way of user device 210 while user device 210 is operating in a paired state. If the proctor surgeon leaves the operating room, user device 210 may transition to operate in a limited paired state in which the proctor surgeon may continue to view an endoscopic video feed by way of user device 210 but is not able to control operations of surgical system 100 by way of user device 210.

In some examples, pairing system 800 may transition a device from operating in a limited paired state to operating in a paired state based on user input. For example, while user device 210 is operating in a limited paired state, the user 208 may provide user input via an application executed by the user device 210 directing the user device 210 to transition to operating in a paired state. In some examples, pairing system 800 may require evidence that the user is in proximity to the medical system prior to transitioning the device to operating in the paired state, such as by scanning a QR code or bar code associated with the medical system, capturing an image of the medical system, etc.

Various operations that may be performed by pairing system 800 (e.g., by processing unit 804 of pairing system 800), and examples of these operations, will now be described. It will be recognized that the operations and examples described herein are merely illustrative of the many different types of operations that may be performed by pairing system 800.

In some examples, pairing system 800 may determine that a device (e.g., user device 210) detects an ultrasonic beacon transmission (e.g., first transmission 304-1) that includes a pilot signal and an encoded information signal. Based on the pilot signal, pairing system 800 may decode the encoded information signal to identify a medical system associated with the ultrasonic beacon transmission. In response to identifying the medical system, pairing system 800 may direct the device to enter into a pairing state in which the device is communicatively paired with the medical system. In this way, a user of the device may interact with medical system by way of the device while it is paired with the medical system. For instance, user 208 may access, by way of user device 210, one or more functional features associated with medical system 206.

However, establishing and maintaining a communicative pairing state between a device and a medical system in a medical facility is often not a simple process. A medical facility is a busy and complex environment. For example, a medical facility may include many different medical systems and many different ultrasonic beacons (see, e.g., FIGS. 5-7). Additionally, various ultrasonic beacons may come and go as medical systems move throughout the medical facility and turn on or turn off, and as different medical procedures start or stop. The user of the device may also move with the device throughout the medical facility. For example, a technician may move back and forth between two or more operating rooms during two concurrent medical procedures. As a result of these variable conditions, the device might detect multiple ultrasonic beacons at the same time, and the ultrasonic beacons that are detected by the device might change. These conditions may result in unwanted changes of the pairing state of the device.

To further complicate management of the pairing state of the device, movement of the device (even slow movement on the order of 1 meter/second) may result in a Doppler shift of the information signal included in ultrasonic beacon transmissions. This may occur, for example, when a user is moving around in an operating room or within the medical facility, or when a beacon generator is moving. In OFDM, where the subcarriers are densely packed, the Doppler shift can make the message unrecoverable. Motion also creates problems related to the changing delays and path lengths during transmission. These issues are particularly severe because of the slow speed of sound relative to motion, short wavelengths, limited near-ultrasonic bandwidth, and challenging acoustic environment in an operating room. The Doppler shift may thus prevent or affect pairing of the device with a medical system.

To address these issues, pairing system 800 is configured to infer an intended pairing state of the device quickly and efficiently and with as little interruption to the user as possible. Accordingly, pairing system 800 may infer the intended pairing state of the device based on various inputs such as a current pairing state of the device, information obtained from detected ultrasonic beacon transmissions (e.g., pilot signals and/or information signals), information about motion of the device, user input, and/or any other suitable information (e.g., user preferences, user histories, predictive information, etc.). Pairing system 800 may use these inputs to determine whether and how the device will transition between different pairing states.

Figure 10:
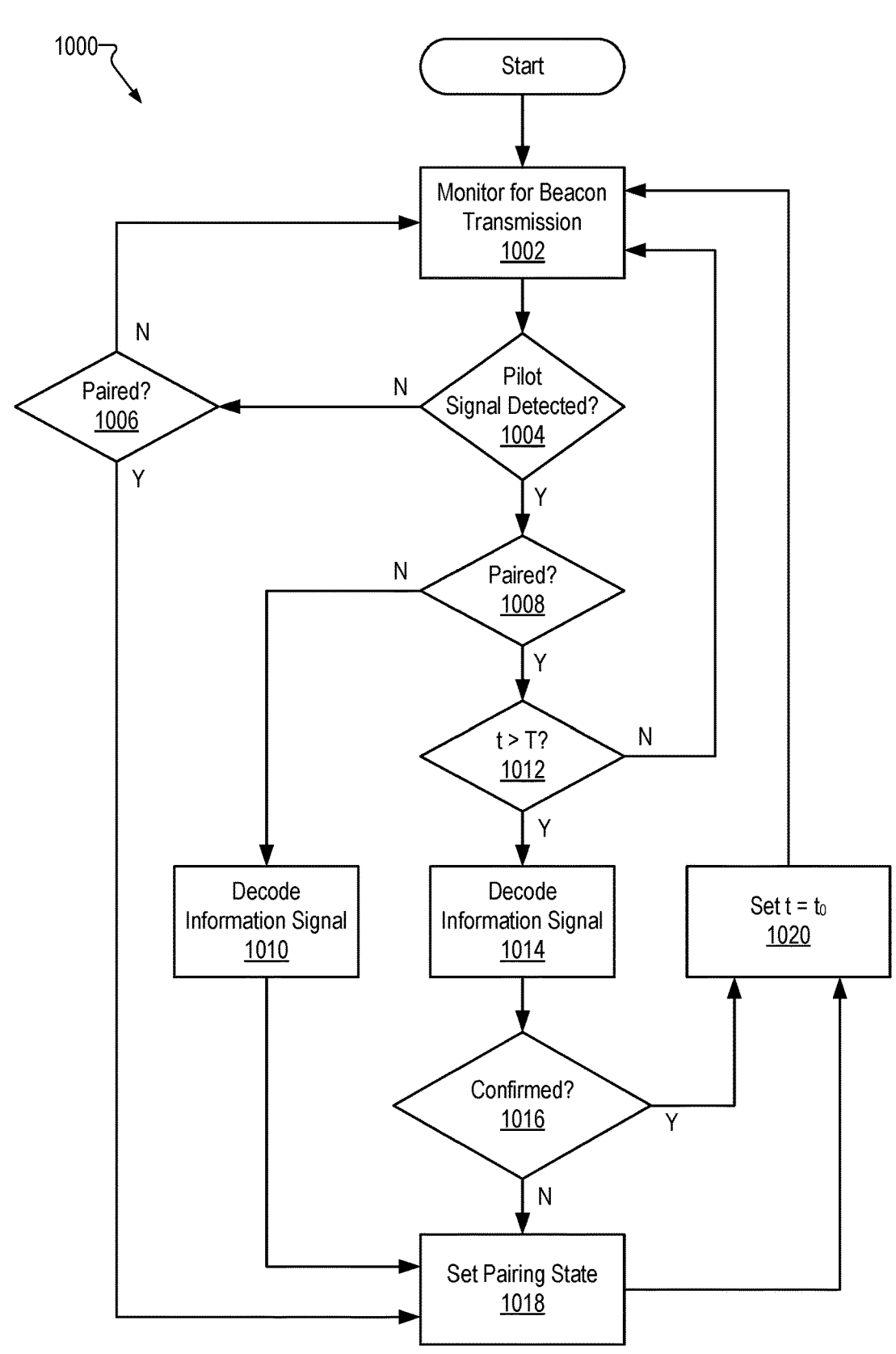
FIG. 10 shows an illustrative method of managing a pairing state of a device.

Ultrasonic beacon-based methods for establishing and managing a pairing state of a device will now be described with reference to FIG. 10. FIG. 10 shows an illustrative method 1000. While FIG. 10 shows illustrative operations according to one embodiment, other embodiments may omit, add to, reorder, combine, and/or modify any of the steps shown in FIG. 10. While the operations shown in FIG. 10 are described as being performed by pairing system 800, it will be understood that the operations may be performed by any components included in pairing system 800 and/or any implementation thereof (e.g., a device such as user device 210, a medical system, a component of a medical system, a combination of devices, a remote computing system, etc.). Method 1000 may begin, for example, when a device is turned on, when the device initiates execution of a particular application, when a user logs into the application executed by the device, when an ultrasonic sensor on the device is turned on, when the device connects to a particular network (e.g., a medical facility network), when the device moves into a particular geographic location (e.g., based on GPS or other location tracking methods), in accordance with a defined schedule, and/or any other suitable event or time.

In operation 1002, pairing system 800 (e.g., by way of an ultrasonic sensor included in the device) monitors for ultrasonic beacon transmissions. Operation 1002 may be performed in any suitable way, including in any way described herein.

In operation 1004, pairing system 800 determines whether the device detects a pilot signal included in an ultrasonic beacon transmission. If pairing system 800 determines that the device does not detect a pilot signal, processing proceeds to operation 1006.

In operation 1006, pairing system 800 checks the current pairing state of the device. If pairing system 800 determines that the device is not paired with any medical system, processing returns to operation 1002 to monitor for ultrasonic beacon transmissions. On the other hand, if pairing system 800 determines that the device is paired (e.g., in a paired state or a limited paired state) with a medical system when the device does not detect any pilot signal, processing proceeds to operation 1018 and transitions the device to operate in a new pairing state for the device (e.g., an unpaired state, a limited paired state, etc.). Operation 1018 will be described below in more detail. Processing then returns to operation 1002 to monitor for subsequent ultrasonic beacon transmissions.

Returning again to operation 1004, if pairing system 800 determines that the device detects a pilot signal in an ultrasonic beacon transmission, processing proceeds to operation 1008.

In operation 1008, pairing system determines a current pairing state of the device. If pairing system 800 determines that the device is not paired with any medical system, processing proceeds to operation 1010.

In operation 1010, pairing system 800 decodes, based on the detected pilot signal, an encoded information signal included in the detected ultrasonic beacon transmission to identify information included in the encoded information signal ((e.g., a medical system associated with the ultrasonic beacon transmission). Operation 1010 may be performed in any suitable way, including any way described herein.

In some examples, pairing system 800 may identify a medical system associated with the ultrasonic beacon by comparing the decoded information in the ultrasonic beacon with medical facility data. The medical facility data may take the form of one or more tables or other data structures that associate various attributes of a medical facility, such as predefined areas within the medical facility, medical systems located within the predefined areas of the medical facility, beacon generators located within the predefined areas of the medical facility, and medical sessions being performed within the medical facility and/or with the medical systems. In some examples, pairing system 800 may be configured to access the medical facility data from a medical facility management system. Alternatively, the medical facility data may be tracked, generated, and/or maintained by pairing system 800 and/or the device.

In some examples, pairing system 800 may identify a medical system that is physically located within the same predefined area as the beacon generator that emitted the ultrasonic beacon. For instance, pairing system 800 may identify, based on medical facility data, a medical system ID that is directly or indirectly associated with a location ID included in the ultrasonic beacon. As another example, pairing system 800 may identify a medical system that is being used to perform a medical session that is represented by a medical session identifier included in the ultrasonic beacon. For instance, pairing system 800 may identify, based on medical facility data, a medical system ID that is directly or indirectly associated with a surgical session ID included in the ultrasonic beacon. As yet another example, pairing system 800 may identify a medical system associated with the beacon generator that emitted the ultrasonic beacon. For instance, pairing system 800 may identify, based on medical facility data, a medical system ID that is directly or indirectly associated with a beacon generator ID included in the ultrasonic beacon. In some examples, pairing system 800 may identify a medical system associated with the ultrasonic beacon by identifying a medical system ID included in the ultrasonic beacon. For example, the beacon generator may be configured to include the medical system ID in the ultrasonic beacon when the medical system and the beacon generator are permanently located within a predefined area, or when the beacon generator is included in the medical system.

After pairing system 800 decodes the encoded information signal to identify the medical system associated with the ultrasonic beacon transmission, processing proceeds to operation 1018. In operation 1018, pairing system 800 sets a new pairing state based on the identified medical system. For example, pairing system 800 may cause the device to enter into a paired state with the medical system.

In some embodiments, pairing of the device with the medical system may be conditioned on authentication of a user associated with the device. For example, a pairing process may not be complete until the user of the device has logged in to the device or to an application or service provided by pairing system 800 and accessible through the device. Additionally or alternatively, successful pairing may further be conditioned on other parameters, such as an identity of the authenticated user matching an identity of a surgical team member previously assigned to a surgical session (e.g., at initiation or creation of the surgical session), or upon the authenticated user successfully providing user input to identify, for example, a surgical session associated with the medical system with which the device is attempting to pair (e.g., by identifying surgical session ID information, etc.). Pairing system 800 may detect such successful authentication in any suitable manner (e.g., by receiving data representative of the successful authentication from the medical system and/or the device).

After transitioning the device from operating in an unpaired to state to operating in a paired state with the medical device, pairing system 800 may initialize a clock to an initial time to in operation 1020 (explained below in more detail), and then processing returns to operation 1002 to monitor for subsequent ultrasonic beacon transmissions.

Returning again to operation 1008, if pairing system 800 determines that the device is paired with a medical system (e.g., in a paired state or a limited paired state), processing proceeds to operation 1012 in which pairing system 800 determines whether to perform a quick "pilot check" or a more robust "confirmation check." The pilot check and the confirmation check are part of a maintenance process performed by pairing system 800 to determine whether to continue operating the device in the paired state (or in a limited paired state).

In operation 1012, pairing system 800 determines whether the device detects the pilot signal within a threshold time T of a pairing state initialization event. A pairing state initialization event may comprise any suitable event associated with establishing or maintaining the device in a paired state (or limited paired state). In some examples, a pairing state initialization event includes the most recent transition between pairing states (e.g., performance of operation 1018) and/or most recent decoding of an encoded information signal included in a detected ultrasonic beacon transmission (e.g., performance of operation 1010 or operation 1014, which will be described below). Additionally or alternatively, a pairing state initialization event may include detection, by pairing system 800, of a particular action performed by the medical system, an interaction by the user with the device to access a functional feature associated with the medical system (e.g., to control operations of the medical system by way of the user device), or any other suitable action. In yet further examples, a pairing state initialization event may include the passage of the threshold time T.

Operation 1012 may be performed in any suitable way. For example, pairing system 800 may determine whether a time t at which the pilot signal is detected is greater than an initial time to plus the threshold time T. The threshold time T may be any suitable time period, such as 1 minute, 30 seconds, 10 seconds, 1 second, 10 milliseconds, etc. Pairing system 800 may set the initial time to when a pairing state initialization event occurs, such as by resetting (initializing) a clock to an initial time to. For instance, as shown in operation 1020, pairing system 800 may reset the clock by setting the current time t to zero (to). In some examples, the threshold time T may be set (either manually or automatically) based on one or more factors, such as the particular medical system or type of medical system, user role or user profile of the user logged in to the device, the device or type of device, current pairing state (e.g., paired state or limited paired state), whether the device is paired with other medical systems, the number and/or frequency of pairing state transition events, and/or any other suitable information.

In operation 1012, if pairing system 800 determines that the threshold time T has not elapsed since the pairing state initialization event (e.g., that the device detects the pilot signal within the threshold time T), the process returns to operation 1002 to monitor for subsequent ultrasonic beacon transmissions. By this pilot check, pairing system 800 causes the device to continue operating in the communicatively paired state based on the detection of the pilot signal of the ultrasonic beacon transmission but without decoding the encoded information signal of the ultrasonic beacon transmission.

If, however, pairing system 800 determines that the threshold time T has elapsed since the pairing state initialization event (e.g., the detection of the pilot signal is not within the threshold time T), processing proceeds to operation 1014.

In operation 1014, pairing system 800 decodes the encoded information signal of the ultrasonic beacon transmission to identify a medical system associated with the ultrasonic beacon transmission. Operation 1014 may be performed in any suitable way, including any way described herein.

In operation 1016, pairing system determines whether the medical system associated with the ultrasonic beacon transmission corresponds to the medical system with which the device is currently paired. Operation 1016 may be performed in any suitable way. For example, pairing system 800 may compare the decoded information from the encoded information signal with the medical facility data to determine whether the device is currently located in the same location as the medical facility with which the device is paired. Operation 1016 may additionally or alternatively include performing an error correction process based on the information signal.

If pairing system 800 determines that the medical system associated with the ultrasonic beacon transmission corresponds to the medical system with which the device is currently paired, processing proceeds to operation 1020 to initialize the clock and then returns to operation 1002 to monitor for subsequent ultrasonic beacon transmissions. By this confirmation check, pairing system 800 causes the device to continue operating in the communicatively paired state based on a confirmation that the medical system associated with the ultrasonic beacon transmission corresponds to the medical system with which the device is currently paired.

If, however, pairing system 800 determines in operation 1016 that the medical system associated with the ultrasonic beacon transmission does not correspond to the medical system with which the device is presently paired, processing proceeds to operation 1018. In operation 1018, pairing system 800 sets a new pairing state based on the medical system associated with the detected ultrasonic beacon transmission. For example, pairing system 800 may transition the device from operating in a paired state with the currently paired medical system to operating in an unpaired state with the medical system, Additionally or alternatively, pairing system 800 may cause the device to enter into a pairing state in which the device is communicatively paired with the medical system associated with the ultrasonic beacon transmission.

Processing then proceeds to operation 1020 to initialize the clock and then returns to operation 1002 to monitor for subsequent ultrasonic beacon transmissions. By this confirmation check, pairing system 800 may transition to a new pairing state when a new medical system is detected. In the new pairing state, the device may be unpaired from any medical system, may pair only with the newly detected medical system, or may be paired with both the presently paired medical system and the newly detected medical system.

In the foregoing process, the pilot check may be performed more frequently than the confirmation check (e.g., with a frequency greater than 1/T) because decoding an encoded information signal consumes more battery power than does detecting a pilot signal Thus, method 1000 accurately infers and intended pairing state and manages the pairing state while conserving battery power.

Various modifications may be made to method 1000 to further refine establishment and management of the pairing state of the device, as will now be described.

For example, rather than performing a confirmation check only in response to a determination that the threshold time T has elapsed since the pairing state initialization event (operation 1012 (Y)), pairing system 800 may additionally or alternatively decode the encoded information signal when some other detected condition indicates a possible change in conditions (e.g., that the device may have moved, another beacon generator has come online, etc.). For example, pairing system 800 may detect a change in quality of the pilot signal (e.g., a drop or increase in SNR), which may occur, for instance, when the device moves farther away from or closer to an ultrasonic beacon generator. In other examples, pairing system 800 may detect a sudden change in timing of pilot signal transmissions, different information encoded in the pilot signal, or any other suitable change in conditions. In response to detecting the change in quality of the pilot signal and/or other changed conditions, pairing system 800 may proceed to operation 1014 and perform the confirmation check. In some examples, detection of the changed conditions may trigger the confirmation check even when the threshold time T has not elapsed since the pairing state initialization event.

In another modification, rather than monitoring only for pilot signals in operation 1004, pairing system 800 may instead monitor for any communication in the ultrasonic range. For example, the pilot signal may be the same as, or a part of, the information signal. Accordingly, pairing system 800 may detect a pilot signal simply by detecting the presence of a transmission in the ultrasonic range.

In some examples, the device does not transition directly from a paired state to an unpaired state if the pilot check or confirmation check fails. Rather, the device may transition from a paired state only to a limited paired state. In additional or alternative examples, the device transitions from a paired state to a limited paired state or an unpaired state only if the pilot check or confirmation check fails a threshold number of consecutive times.

In some examples, operation 1012 is omitted from method 1000 so that pairing system 800 does not perform a pilot check. In these examples, the device continues operating in the current pairing state only upon a successful confirmation check.

Figure 11:
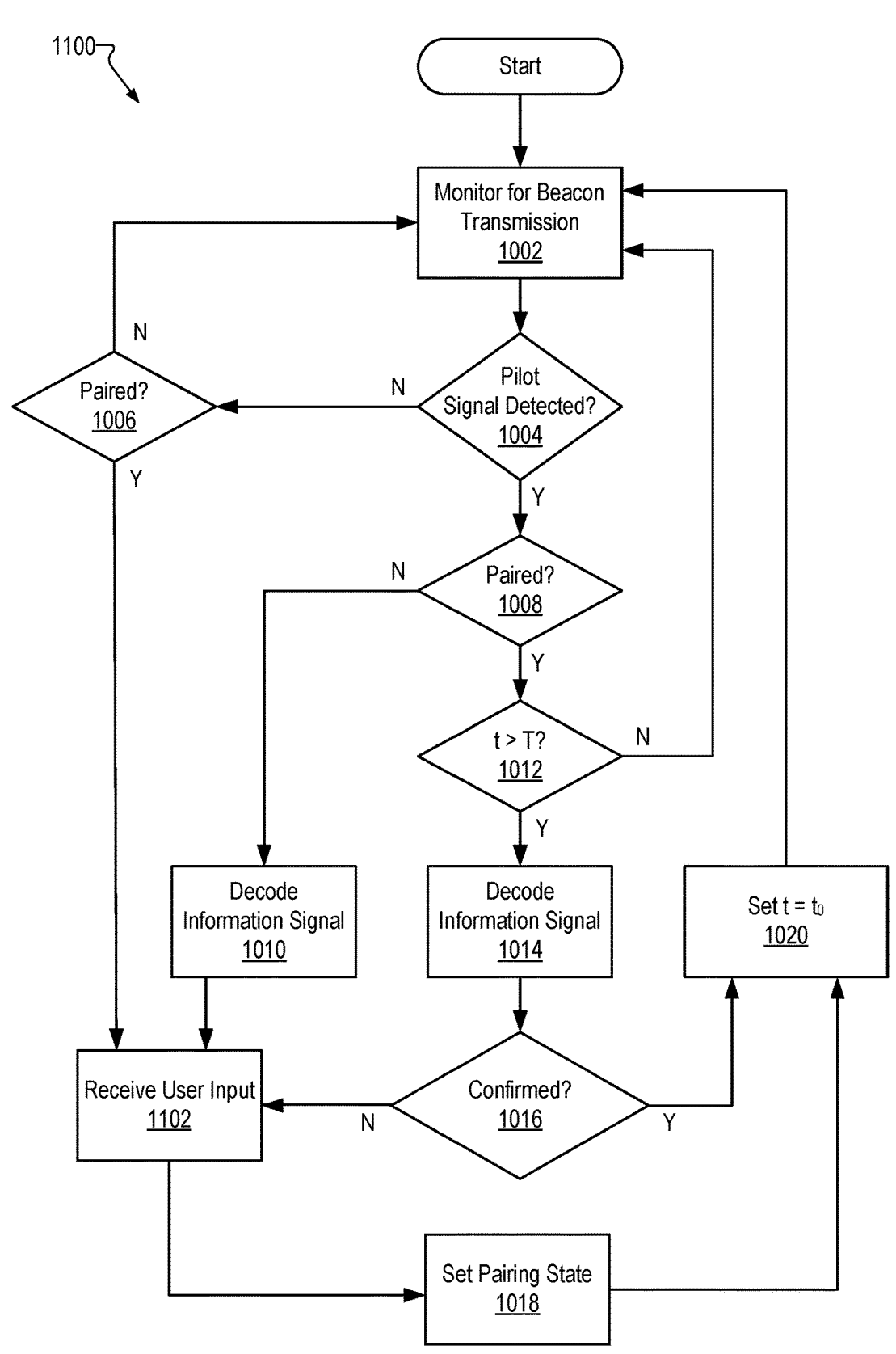
FIG. 11 shows another illustrative method of managing a pairing state of a device.

In yet further examples, operation 1018 may be performed based on user input, as shown in FIG. 11, FIG. 11 shows a method 1100 that is similar to method 1000 except that method 1100 includes an operation 1102 prior to performing operation 1018.

In operation 1102, pairing system 800 receives user input indicating a desired pairing state of the device, and in operation 1018 pairing system sets the pairing state based on the received user input. The user input may be received in any suitable way. For example, pairing system 800 may prompt the user, by way of the device (e.g., by way of a graphical user interface, by an audio or haptic notification, or the like), to provide input in response to any one or more of operation 1006 (Y), operation 1010, and operation 1016 (N). The device may be configured to receive the user input in any suitable way, such as by touch input, voice command, or motion gesture of the device.

To illustrate, if operation 1102 is reached from operation 1006 (no pilot signal detected while operating in a paired state) or operation 1016 (confirmation failed while operating in a paired state), the user input may indicate a desire to maintain operation of the device in the paired state even though no ultrasonic beacon transmission is detected. Accordingly, in operation 1018 pairing system 800 may set the device to continue operating in the paired state or in a limited paired state.

If operation 1102 is reached from operation 1010, the user may be prompted to confirm, by user input by way of the device, a desire to pair the device with the medical system associated with the ultrasonic beacon transmission.

Operation 1102 may assist pairing system 800 to determine an appropriate pairing state when the device detects multiple different ultrasonic beacons. In some examples, method 1100 is performed when the device detects multiple different ultrasonic beacons, and method 1000 is performed when the device detects only one ultrasonic beacon.

While FIG. 11 shows that operation 1102 may be performed in response to operations 1006 (N), 1010, and 1016 (Y), operation 1102 may be performed in response to more or fewer operations and/or any other operations as may serve a particular implementation (e.g., operation 1008 (N)).

In yet further modifications of methods 1000 and 1100, operation 1018 may further be performed based on preferences or a profile of the user or a role of the user (e.g., surgeon, nurse, technician, etc.). For example, a user may specify particular preferences for transitioning between pairing states. Additionally or alternatively, an administrator of pairing system 800 may limit certain functional features that may be accessed by way of the user device based on the user or user role.

Figure 12A:
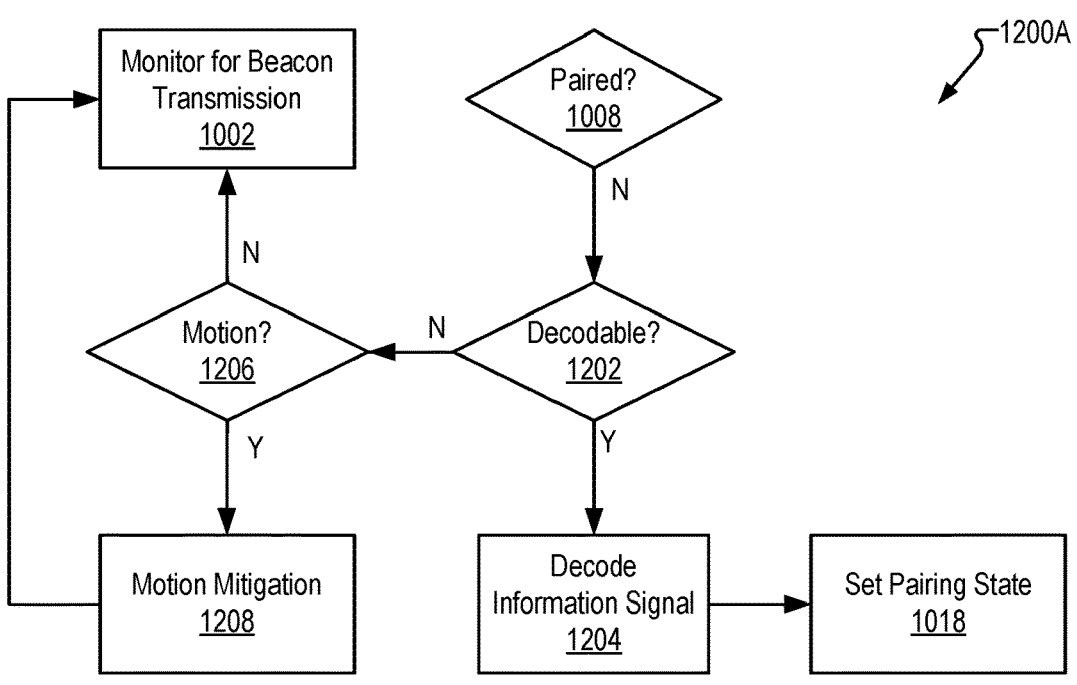
FIGS. 12A and 12B show illustrative alternative operations that may be included in the methods of FIGS. 10 and 11.
Figure 12B:
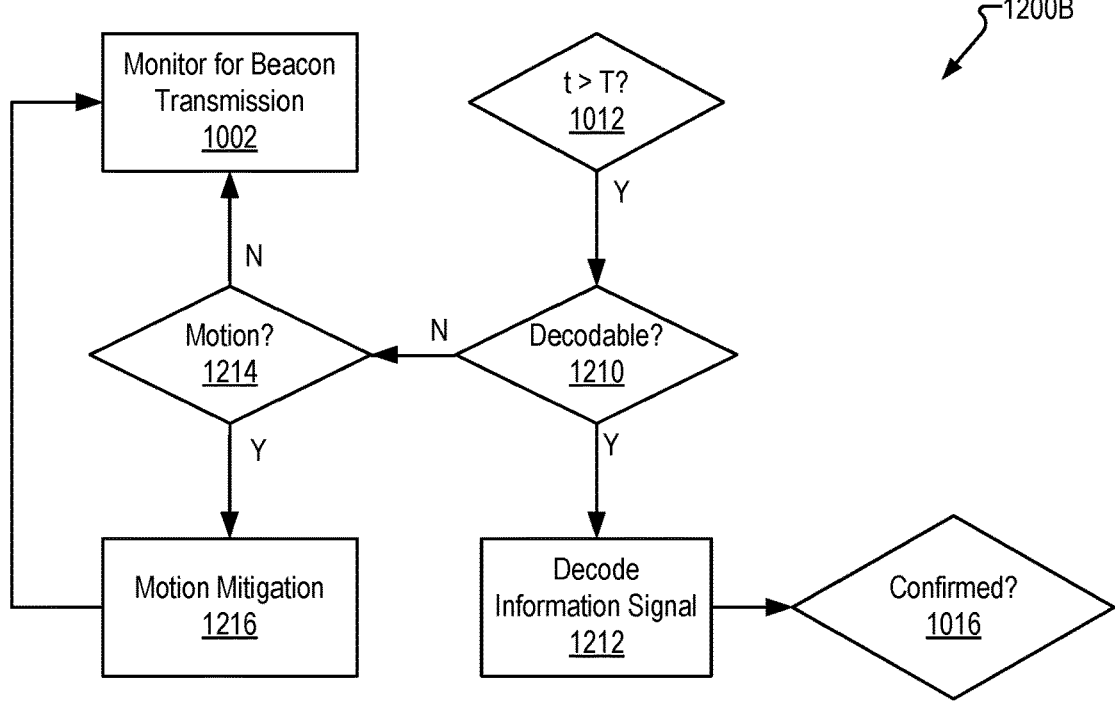

As mentioned above, motion of the device may also generate a Doppler effect in the encoded information signal of an ultrasonic beacon transmission, making the encoded information signal unrecoverable. Accordingly, the device may be unable to pair with the medical system associated with the ultrasonic beacon transmission, and the confirmation check may fail, resulting in an unintended unpairing of the device. Accordingly, pairing system 800 may also be configured to use motion detection in the maintenance process and/or to set the pairing state of the device. Accordingly, operation 1010 in FIGS. 10 and 11 may be substituted as shown in FIG. 12A. Additionally or alternatively, operation 1014 in FIGS. 10 and 11 may be substituted as shown in FIG. 12B.

FIG. 12A shows illustrative alternative operations 1202 to 1208 that may be substituted for operation 1010 in FIGS. 10 and 11.

Operation 1202 is performed after operation 1008 (N). In operation 1202, when the device is attempting to pair with a new medical system, pairing system 800 may determine whether the encoded information signal of the detected ultrasonic beacon transmission is decodable. Operation 1202 may be performed in any suitable way, such as by a parity check, an error check, validation of the decoded information against reference information (e.g., medical facility data), or any other suitable validation method.

If pairing system 800 determines that the encoded information signal is decodable, pairing system 800 decodes the encoded information signal in operation 1204 and then proceeds to operation 1018, which may be performed as described above to communicatively pair the device with the medical system associated with the ultrasonic beacon transmission.

If, however, pairing system 800 determines that the encoded information signal is not decodable, processing proceeds to operation 1206. In operation 1206, pairing system 800 determines whether the device is in motion. Operation 1206 may be performed in any suitable way. In some examples, pairing system 800 may determine that the device is in motion based on information generated by one or more motion sensors included in the device and configured to detect motion of the device. The motion sensor(s) may include, for example, an inertial measurement unit (WU), an accelerometer, a gyroscope, a magnetometer, and/or any other suitable motion sensing device. Additionally or alternatively, pairing system 800 may process the encoded information signal to identify the Doppler shift in the encoded information signal.

If pairing system 800 determines that the device is not in motion, processing may return to operation 1002, which may be performed as described above to monitor for subsequent ultrasonic beacon transmissions. Additionally or alternatively, pairing system 800 may perform any other operations configured to improve reception and/or decoding of the encoded information signal, such as adjusting frequency filters or algorithms used to process encoded information signal.

If, however, pairing system 800 determines that the device is in motion, processing proceeds to operation 1208. In operation 1208, pairing system 800 performs a motion mitigation process. In some examples, the motion mitigation process includes providing a notification to the user indicating that pairing was unsuccessful due to motion and/or instructing the user to hold the device still so the device can be paired. Additionally or alternatively, the motion mitigation process may include providing alternate means for pairing the device with the medical system. The alternate means may include any suitable means configured to establish that the device is in physical proximity to the medical system, such as a barcode, a QR code, an RFID tag, image recognition, user input, and the like. Additionally or alternatively, motion mitigation may comprise not attempting to pair while the device is in motion. In some examples, motion mitigation may include implementing changes to transmission or reception protocols, such as spacing out subchannel frequencies (refer to FIG. 3) or storing and combining more ultrasonic beacon transmissions (e.g., transmissions 304) together at the device. Such techniques may make pairing more robust at the expense of a slightly increased pairing time. In yet further examples, motion mitigation may include performing a Doppler correction of the corrupted information signal. Doppler correction may be performed in any suitable way.

Upon performing operation 1208, processing returns to operation 1002, which may be performed as described above to monitor for subsequent ultrasonic beacon transmissions.

FIG. 12B shows illustrative alternative operations 1210 to 1216 that may be substituted for operation 1014 in FIGS. 10 and 11.

Operation 1210 is performed after operation 1012 (Y) when pairing system 800 is attempting to confirm that the medical system associated with the detected ultrasonic beacon corresponds to the medical system device with which the device is presently paired. In operation 1210, pairing system 800 may determine whether the encoded information signal of the detected ultrasonic beacon transmission is decodable. Operation 1202 may be performed in any suitable way, including any way described herein.

If pairing system 800 determines that the encoded information signal is decodable, pairing system 800 decodes the encoded information signal in operation 1212 and then proceeds to operation 1016, which may be performed as described above.

If, however, pairing system 800 determines that the encoded information signal is not decodable, processing proceeds to operation 1214. In operation 1214, pairing system 800 determines whether the device is in motion. Operation 1214 may be performed in any suitable way, including in any way described herein.

If pairing system 800 determines that the device is not in motion, processing may return to operation 1002, which may be performed as described above to monitor for subsequent ultrasonic beacon transmissions. Additionally or alternatively, pairing system 800 may perform any other operations configured to improve reception and/or decoding of the encoded information signal, such as adjusting frequency filters or algorithms used to process encoded information signal.

If, however, pairing system 800 determines that the device is in motion, processing proceeds to operation 1216. In operation 1216, pairing system 800 performs a motion mitigation process. Operation 1216 may be performed in any suitable way and may be similar to operation 1208 described above. For example, operation 1216 may comprise providing a notification to the user indicating that confirmation of pairing cannot be performed due to motion and/or instructing the user to hold the device still for the confirmation check, providing alternate means (as described above) for confirming the paired state of the device, not attempting to confirm the paired state of the device while the device is in motion, implementing changes to transmission or reception protocols, and/or performing a Doppler correction of the corrupted information signal. In additional or alternative examples, operation 1216 may comprise transitioning the device to operate in a limited paired state, as described above.

In yet further examples, the motion mitigation process may include modifying one or more parameters to prevent unpairing while the device is in motion. For example, the motion mitigation process may comprise initializing the clock (e.g., setting the current time $t=t_0$ or to some other earlier time) and/or increasing the threshold time T.

In some examples, pairing system 800 may count a number of consecutive occurrences of an undecodable beacon (operation 1202 (N) and/or operation 1210 (N)) and/or a number of occurrences of motion detection and, in response, may perform an additional mitigation action. The additional mitigation action may include, for example, transitioning the device to operate in a new pairing state (e.g., an unpaired state, a limited paired state, etc.), requesting user input to indicate the appropriate pairing state, and/or any of the mitigation actions previously described.

Upon performing operation 1216, processing returns to operation 1002, which may be performed as described above to monitor for subsequent ultrasonic beacon transmissions.

Figure 13:
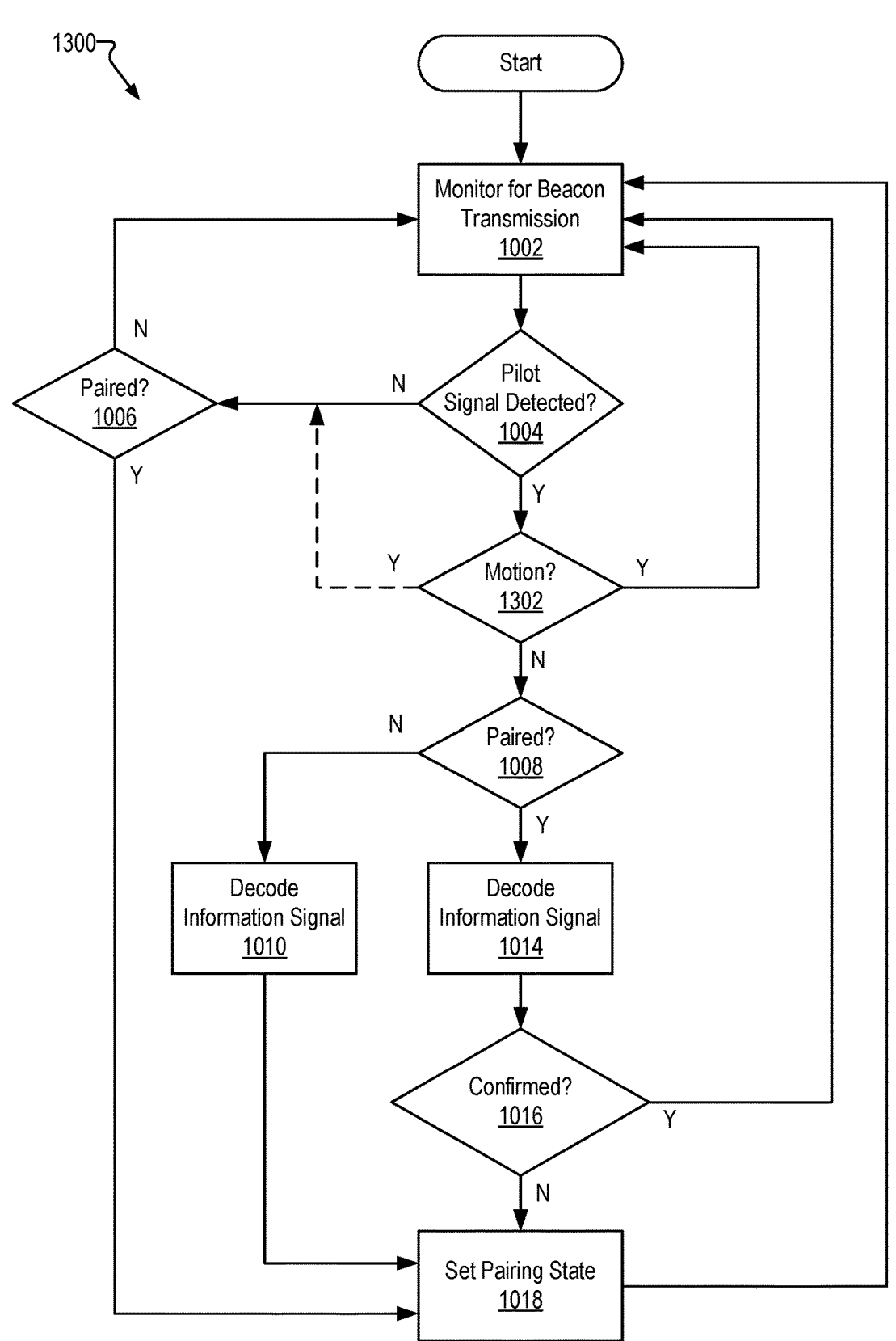
FIG. 13 shows another illustrative method of managing a pairing state of a device.

FIG. 13 shows another illustrative method 1300 that accounts for device motion. Method 1300 is similar to method 1000 except that in method 1300 an operation 1302 has been added and operations 1012 and 1020 have been removed.

In operation 1302, pairing system 800 determines whether the device is in motion. Operation 1302 may be performed in any suitable way, including any way described herein.

If pairing system 800 determines that the device is in motion, processing returns to operation 1002 to continue monitoring for ultrasonic beacon transmissions. Accordingly, pairing system 800 does not attempt to communicatively pair or confirm a paired state of the device while the device is in motion.

In an alternative configuration of method 1300, processing proceeds to operation 1006, as indicated by the dashed line, if pairing system 800 determines that the device is in motion. Thus, when the device is currently unpaired (operation 1006 (N)), pairing system 800 does not attempt to communicatively pair the device while the device is in motion.

On the other hand, when the device is currently paired (operation 1006 (Y)), processing proceeds to operation 1018. In operation 1018, pairing system 800 may set the device to operate in a limited paired state while the device is in motion. In this way, pairing system 800 maintains the device operating in a paired state based on detection of the pilot signal but prevents potentially undesired actions that may be taken by the user by setting the device to the limited paired state while the device is in motion.

Returning again to operation 1302, if pairing system 800 determines that the device is not in motion, processing proceeds to operation 1008, which may be performed as described above to determine whether the device is presently paired with a medical system. Pairing system 800 may then either proceed to communicatively pair the device with a medical system (operations 1010 and 1018) or perform a confirmation check (operations 1014 and 1016).

Certain foregoing embodiments have described establishing and/or managing a pairing state of a device with respect to a single medical system based on a single detected ultrasonic beacon. In other embodiments, pairing system 800 may be configured to pair or manage a paired state of a device with one or more medical systems based on detection of multiple ultrasonic beacons. For example, as described above and as shown in FIGS. 5 and 6, medical facility 202 may include multiple beacon generators 212 within predefined area 204 and/or included in medical system 206, and, as shown in FIG. 7, medical facility 202 may include additional beacon generators 712 located outside of predefined area 204 (e.g., within predefined area 704). Methods 1000, 1100, and 1300 may be used in such multi-beacon configurations.

In some examples, pairing system 800 is configured to pair or confirm a pairing state of a device with a medical system only if pairing system 800 determines that the device detects a set of multiple ultrasonic beacons associated with a particular medical system. For example, in operation 1004 of methods 1000, 1100, and/or 1300, pairing system 800 may determine that the device detects multiple distinct pilot signals of multiple different ultrasonic beacon transmissions (e.g., ultrasonic beacon transmissions of different ultrasonic beacons). If the device is not in a paired state (operation 1008 (N)), or if the device is in a paired state and the pilot signals are detected after the threshold time T (operation 1012 (Y)), pairing system 800 may decode the encoded information signals of each ultrasonic beacon transmission to identify a medical system associated each of the detected ultrasonic beacon transmissions (operation 1010). In operation 1018, pairing system 800 may set the pairing state of the device or confirm the pairing state based on the information included in the decoded encoded information signals.

For example, pairing system 800 may pair or confirm a pairing state of the device with a medical system that is associated with two or more of the detected ultrasonic beacon transmissions. For instance, with reference to FIGS. 5-7, pairing system 800 may communicatively pair or maintain a paired state of user device 210 with medical system 206 only if pairing system 800 determines that user device 210 detects any two or more of ultrasonic beacons 214-1 through 214-3.

In other examples, pairing system 800 may pair or confirm a pairing state of the device with a medical system only if pairing system 800 determines that the device detects the set of all ultrasonic beacons associated with the medical system. For instance, with reference to FIGS. 5-7, pairing system 800 may communicatively pair or maintain a paired state of user device 210 with medical system 206 only if pairing system 800 determines that user device 210 detects all ultrasonic beacons 214 (e.g., ultrasonic beacons 214-1 through 214-3) associated with medical system 206. If pairing system 800 determines that user device 210 does not detect all ultrasonic beacons 214 associated with medical system 206, pairing system 800 does not communicatively pair user device 210 with medical system 206 (or pairs user device 210 in a limited paired state with medical system 206) or determines that the confirmation check has failed and proceeds to operation 1018 (e.g., transitions to an unpaired state or a limited paired state).

In some examples, the set of ultrasonic beacons comprises all ultrasonic beacons included in components of the medical system. For instance, the set of ultrasonic beacons may include a unique component identifier (encoded in the information signal in each ultrasonic beacon transmission) for each component included in the medical system. In this way, pairing system 800 does not pair the device with the medical system unless pairing system 800 determines that the device has detected an ultrasonic beacon associated with each component of the medical system (e.g., an ultrasonic beacon included in manipulating system 102, an ultrasonic beacon included in user control system 104, and an ultrasonic beacon included in auxiliary system 106). Pairing system 800 may determine whether a device detects a set of all ultrasonic beacons associated with a medical system in any suitable way. For example, pairing system 800 may refer to medical facility data to determine whether the device detects all ultrasonic beacons associated with a particular medical system.

In some examples, pairing system 800 may condition pairing or confirmation of a pairing state of a device with a medical system on a determination that the device does not detect any ultrasonic beacons that are not associated with the currently paired medical system. For instance, as shown with reference to FIG. 7, pairing system 800 may communicatively pair or confirm pairing of user device 210 with medical system 206 only if pairing system 800 determines that user device 210 does not detect any ultrasonic beacons other than ultrasonic beacons 214 (e.g., any of ultrasonic beacons 714-1 through 714-3). If pairing system 800 determines that user device 210 detects any ultrasonic beacon 714, and even if user device 210 detects one or more (or all) ultrasonic beacons 214, pairing system 800 does not communicatively pair user device 210 with medical system 206 (or pairs user device 210 in a limited paired state with medical system 206) or determines that the confirmation check has failed and proceeds to operation 1018 (e.g., transitions to an unpaired state or a limited paired state).

In yet further examples, pairing system 800 may pair a device with a medical system in a limited paired state if pairing system 800 determines that the device detects ultrasonic beacons not associated with the currently paired medical system. For instance, as shown with reference to FIG. 7, pairing system 800 may communicatively pair user device 210 with medical system 206 in a limited paired state if pairing system 800 determines that user device 210 detects ultrasonic beacons associated with medical system 706 (e.g., any of ultrasonic beacons 714-1 through 714-3). If pairing system 800 determines that user device 210 detects any ultrasonic beacon 714, pairing system 800 does not communicatively pair user device 210 with medical system 206, even if user device 210 detects one or more (or all) ultrasonic beacons 214.

In additional or alternative examples, in operation 1018 pairing system 800 may pair a device with a medical system that is associated with the most ultrasonic beacons detected by the device. For example, pairing system 800 may pair user device 210 with medical system 206 in response to determining that user device 210 detects three ultrasonic beacons (e.g., ultrasonic beacons 214-1 through 214-3) associated with medical system 206 and detects only two ultrasonic beacons (e.g., ultrasonic beacons 714-1 and 714-2) associated with medical system 706.

In any of the examples described herein, pairing or confirming a pairing state of a device may also be based on a signal strength of the detected ultrasonic beacons. For example, pairing system 800 may pair or confirm a pairing of a device with a medical system only if the signal strengths of the ultrasonic beacons associated with the medical system exceed a predetermined threshold.

Referring again to operation 1008, if the device is in a paired state or a limited paired state (operation 1008 (Y)) after detecting multiple pilot signals and the pilot signals are detected within the threshold time T (operation 1012 (N)), then pairing system 800 may maintain operation of the apparatus in the current paired state and return to operation 1002 to monitor for subsequent ultrasonic beacon transmissions. In some examples, pairing system 800 may maintain operation of the apparatus in the currently paired state only if the number of pilot signals detected in operation 1004 corresponds to (e.g., matches, or is equal to or greater than, or is within a certain number of) the number of ultrasonic beacons required for initially pairing the device with the medical system. For instance, as shown with reference to FIG. 7, if user device 210 is paired with medical system 206 based on detection of ultrasonic beacons 214-1 to 214-3, user device 210 may continue operating in the paired state with medical system 206 if user device 210 detects at least three pilot signals, or if user device 210 detects only three pilot signals.

In some examples, if the device detects fewer than a necessary number of pilot signals (e.g., operation 1004 (N)) while operating in a paired state (operation 1006 (Y)), pairing system 800 may set, in operation 1018, a new pairing state based on the number of pilot signals detected (e.g., transition to a limited paired state if some but not all pilot signals are detected).

In the methods and examples described above, pairing system 800 may establish and manage a pairing state of a device with respect to a single medical system. In some examples, pairing system 800 may establish and manage a pairing state of a device with respect to multiple medical systems simultaneously. For instance, a technician may move between multiple operating rooms and an equipment room while multiple medical procedures are being performed concurrently. Accordingly, the device may detect ultrasonic beacon transmissions associated with multiple different medical systems. Pairing system 800 may be configured to use the current pairing state and any other suitable inputs to determine a proper pairing state of the device even when multiple different ultrasonic beacons are detected.

For example, as shown in FIG. 11 pairing system 800 may rely on user input (operation 1102) to determine which medical system or systems to pair with the device. Additionally or alternatively, pairing system 800 may set a pairing state based on the signal strength of the detected ultrasonic beacons. For instance, as shown in FIG. 7, a signal strength of ultrasonic beacons 214-1 to 214-3 detected by user device 210 may be stronger than a signal strength of ultrasonic beacons 712-1 to 712-3. Accordingly, pairing system 800 may pair user device 210 with medical system 206 and not with medical system 706. Alternatively, pairing system 800 may pair user device 210 in a paired state with medical system 206 and in a limited paired state with medical system 706.

In some examples, pairing system 800 may default to maintain the currently paired state rather than transition to a new paired state. For instance, as shown in FIG. 7, user device 210 may be in a paired state with medical system 206 when medical system 706 comes online and ultrasonic beacons 714 are first transmitted. If user device 210 now also detects ultrasonic beacons 714, pairing system 800 may maintain user device in a paired state with medical system 206. Of course, other default settings may be set and may be changed by the user. For example, pairing system 800 may default to request user input and/or transition the user device to operate in a limited paired state with medical system 206 and/or medical system 706.

In some examples, pairing system 800 may rely on unprompted user input to determine which medical system or systems to pair with the device. For instance, as shown in FIG. 7, user device 210 may be operating in a paired state with medical system 206 and may also detect ultrasonic beacons 714. If the user attempts to access a functional feature associated with medical system 206, pairing system 800 may infer that user 208 and user device 210 are located in proximity to medical system 206 and thus may continue operation of user device 210 in a paired state with medical system 206. As another example, if the user attempts to access a functional feature associated with medical system 206 while user device 210 detects ultrasonic beacons 714, pairing system 800 may request user input specifying a desired pairing state of user device with respect to medical system 206 and medical system 706.

In some alternative examples of the methods described above, an ultrasonic beacon may not be associated with a medical system. For example, the ultrasonic beacon may be associated with a particular location within the medical facility that is not associated with a particular medical system, such as a hallway, a break room, an equipment room, a cafeteria, an office, or a lab room. In these examples, pairing system 800 may use the decoded information signal of such ultrasonic beacon transmission as another input to determine an appropriate pairing state. For example, as shown in FIG. 2, user device 210 may be paired with medical system 206 while user device 210 is located within predefined area 204. If user 208 leaves predefined area 204 and carries user device 210 into a break room, user device 210 may detect an ultrasonic beacon associated with the break room but no longer detect ultrasonic beacon 214 associated with medical system 206. Accordingly, pairing system 800 may set the pairing state (operation 1018) based on the determination that user 208 is located in the break room. For example, pairing system 800 may transition user device 208 to operate in a limited paired state with medical system 206 so that user 208 may continue to receive and view information associated with the medical procedure occurring in predefined area 204. Alternatively, pairing system 800 may unpair user device 208 from medical system 206 or may maintain the paired state. In yet further examples, pairing system 800 may prompt the user to provide user input indicating the desired pairing state and may set the pairing state based on the user input.

The foregoing configurations and embodiments have focused on ultrasonic beacon-based systems. However, the present disclosure is not limited to these configurations and embodiments, as various modifications and changes may be made thereto without departing from the scope of the inventive principles described herein. For example, the systems and methods described herein may be based additionally or alternatively on any other suitable beacon or other push notifications, such as electromagnetic signals (e.g., infrared, radio-frequency identification (RFD), etc.), wireless data signals (e.g., Bluetooth, near-field communication, Wi-Fi, etc.), offline data transfer, and the like. Additionally or alternatively, the systems and methods described herein may be used in facilities and environments other than a medical facility, such as recreational facilities (e.g., amusement parks, sports stadiums, parks, etc.), educational facilities (e.g., schools, universities, etc.), shopping centers, business facilities (e.g., offices, research parks, etc.), laboratories, manufacturing facilities, transportation facilities (e.g., airports, train stations, etc.), and the like.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Illustrative non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Illustrative volatile storage media include, but are not limited to, RAM (e.g., dynamic RAM).

Figure 14:
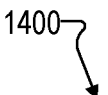
FIG. 14 shows an illustrative computing device.
Figure 14:
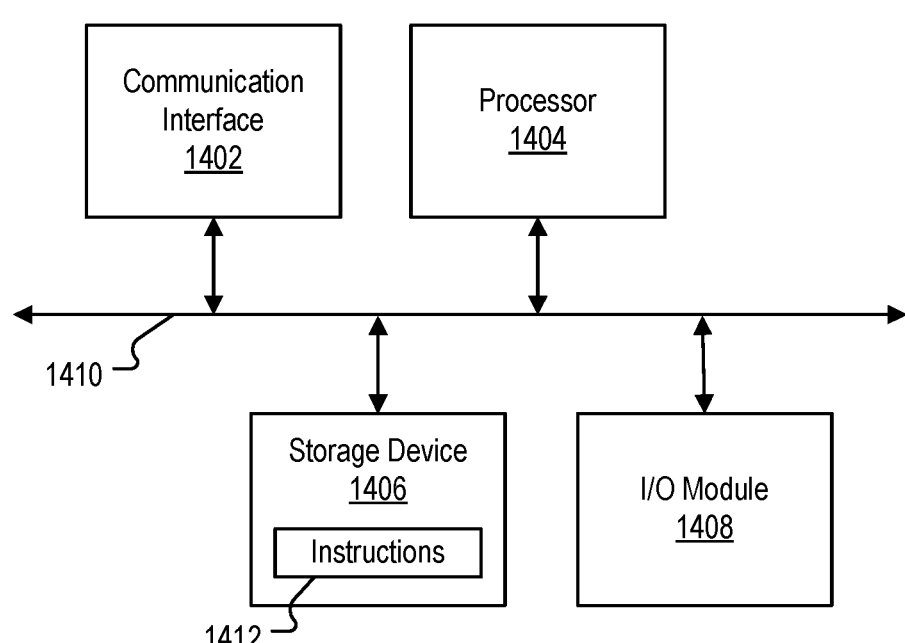

FIG. 14 shows an illustrative computing device 1400 that may be specifically configured to perform one or more of the processes described herein. Any of the systems, units, computing devices, and/or other components described herein may be implemented by computing device 1400.

As shown in FIG. 14, computing device 1400 may include a communication interface 1402, a processor 1404, a storage device 1406, and an input/output ("I/O") module 1408 communicatively connected one to another via a communication infrastructure 1410, While an illustrative computing device 1400 is shown in FIG. 14, the components illustrated in FIG. 14 are not intended to be limiting. Additional or alternative components may be used in other embodiments.

Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data and/or interpreting, executing, and/or directing execution of one or more of the instructions, processes, and/or operations described herein. Processor 1404 may perform operations by executing computer-executable instructions 1412 (e.g., an application, software, code, and/or other executable data instance) stored in storage device 1406.

Storage device 1406 may include one or more data storage media, devices, or configurations and may employ any type, form, and combination of data storage media and/or device. For example, storage device 1406 may include, but is not limited to, any combination of the non-volatile media and/or volatile media described herein. Electronic data, including data described herein, may be temporarily and/or permanently stored in storage device 1406. For example, data representative of computer-executable instructions 1412 configured to direct processor 1404 to perform any of the operations described herein may be stored within storage device 1406. In some examples, data may be arranged in one or more databases residing within storage device 1406.

I/O module 1408 may include one or more I/O modules configured to receive user input and provide user output. I/O module 1408 may include any hardware, firmware, software, or combination thereof supportive of input and output capabilities. For example, I/O module 1408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An apparatus comprising:

one or more processors; and memory storing executable instructions that, when executed by the one or more processors, cause the apparatus to:

detect a first pilot signal included in a first ultrasonic beacon transmission, the first ultrasonic beacon transmission further including a first encoded information signal;

decode, based on the first pilot signal, the first encoded information signal to identify a first medical system associated with the first ultrasonic beacon transmission;

enter, based on the decoding of the first encoded information signal, into a first pairing state in which the apparatus is communicatively paired with the first medical system;

detect, while operating in the first pairing state and within a threshold time of entering the first pairing state, a second pilot signal included in a second ultrasonic beacon transmission, the second ultrasonic beacon transmission further including a second encoded information signal; and continue, based on the detection of the second pilot signal within the threshold time, operating in the first pairing state without decoding the second encoded information signal.

2. The apparatus of claim 1, wherein the instructions, when executed by the one or more processors, further cause the apparatus to:

determine that the apparatus does not detect any pilot signals within the threshold time and subsequent to the detection of the second pilot signal; and transition, based on the determination that the apparatus does not detect any pilot signals within the threshold time and subsequent to the detection of the second pilot signal, from operating in the first pairing state to operating in a second pairing state that is different from the first pairing state.

3. The apparatus of claim 2, wherein the apparatus is communicatively unpaired from the first medical system while operating in the second pairing state.

4. The apparatus of claim 2, wherein:

a functional feature associated with the first medical system is accessible by way of the apparatus while the apparatus operates in the first pairing state; and the functional feature associated with the first medical system is not accessible by way of the apparatus while the apparatus operates in the second pairing state.

5. The apparatus of claim 2, wherein the instructions, when executed by the one or more processors, further cause, based on the determination that the apparatus does not detect any pilot signals and subsequent to the detection of the second pilot signal, the apparatus to request user input to indicate a desired pairing state; and wherein the second pairing state is set based on the user input.

6. The apparatus of claim 1, wherein the instructions, when executed by the one or more processors, further cause the apparatus to:

detect, while operating in the first pairing state and after the threshold time of entering the first pairing state, a third pilot signal included in a third ultrasonic beacon transmission, the third ultrasonic beacon transmission further including a third encoded information signal;

decode, based on the third pilot signal, the third encoded information signal to identify a medical system associated with the third ultrasonic beacon transmission;

determine that the medical system associated with the third ultrasonic beacon transmission corresponds to the first medical system; and continue, based on the determination that the medical system associated with the third ultrasonic beacon transmission corresponds to the first medical system, to operate in the first pairing state.

7. The apparatus of claim 1, wherein the instructions, when executed by the one or more processors, further cause the apparatus to:

detect, while operating in the first pairing state and after the threshold time of entering the first pairing state, a third pilot signal included in a third ultrasonic beacon transmission, the third ultrasonic beacon transmission further including a third encoded information signal;

decode, based on the third pilot signal, the third encoded information signal to identify a medical system associated with the third ultrasonic beacon transmission;

determine that the medical system associated with the third ultrasonic beacon transmission corresponds to a second medical system that is different from the first medical system; and transition, based on the determination that the medical system associated with the third ultrasonic beacon transmission corresponds to the second medical system, from operating in the first pairing state to operating in a third pairing state that is different from the first pairing state.

8. The apparatus of claim 1, wherein the instructions, when executed by the one or more processors, further cause the apparatus to:

detect, while operating in the first pairing state and after the threshold time of entering the first pairing state, a fourth pilot signal included in a fourth ultrasonic beacon transmission, the fourth ultrasonic beacon transmission further including a fourth encoded information signal;

determine that the fourth encoded information signal is not decodable;

determine, based on the determination that the fourth encoded information signal is not decodable, that the apparatus is in motion while the apparatus detects the fourth pilot signal; and continue, based on the determination that the apparatus is in motion while the apparatus detects the fourth pilot signal, to operate in the first pairing state without decoding the fourth encoded information signal.

9. The apparatus of claim 8, further comprising:

an inertial measurement unit;

wherein the determination that the apparatus is in motion while the apparatus detects the fourth pilot signal is based on information generated by the inertial measurement unit.

10. The apparatus of claim 8, wherein the determining that the apparatus is in motion while the apparatus detects the fourth pilot signal comprises identifying a Doppler shift in the fourth encoded information signal.

11. An apparatus comprising:

an ultrasonic sensor configured to detect ultrasonic signals; and a processing unit configured to:

determine that the ultrasonic sensor detects, while the apparatus is operating in a first pairing state in which the apparatus is communicatively paired with a first medical system, a first pilot signal included in a first ultrasonic beacon transmission, the first ultrasonic beacon transmission further including a first encoded information signal identifying a medical system associated with the first ultrasonic beacon transmission;

determine that the ultrasonic sensor detects the first pilot signal within a threshold time of a pairing state initialization event; and control, based on the determination that the apparatus detects the first pilot signal within the threshold time of the pairing state initialization event and without decoding the first encoded information signal, the apparatus to continue operating in the first pairing state.

12. The apparatus of claim 11, wherein the processing unit is further configured to:

determine that the ultrasonic sensor does not detect any pilot signals within the threshold time of the pairing state initialization event and subsequent to the detection of the first pilot signal; and transition, based on the determination that the ultrasonic sensor does not detect any pilot signals within the threshold time of the pairing state initialization event and subsequent to the detection of the first pilot signal, the apparatus from operating in the first pairing state to operating in a second pairing state that is different from the first pairing state.

13. The apparatus of claim 11, wherein the processing unit is further configured to:

determine that the ultrasonic sensor detects, while the apparatus is operating in the first pairing state, a second pilot signal included in a second ultrasonic beacon transmission that is subsequent to the first ultrasonic beacon transmission, the second ultrasonic beacon transmission further including a second encoded information signal identifying a medical system associated with the second ultrasonic beacon transmission;

determine that the ultrasonic sensor detects the second pilot signal after the threshold time of the pairing state initialization event;

decode, based on the second pilot signal and based on the determination that the ultrasonic sensor detects the second pilot signal after the threshold time of the pairing state initialization event, the second encoded information signal to identify the medical system associated with the second ultrasonic beacon transmission;

control, based on a determination that the medical system associated with the second ultrasonic beacon transmission corresponds to the first medical system, the apparatus to continue operating in the first pairing state; and transition, based on a determination that the medical system associated with the second ultrasonic beacon transmission does not correspond to the first medical system, the apparatus from operating in the first pairing state to operating in a second pairing state that is different from the first pairing state.

14. The apparatus of claim 11, wherein the pairing state initialization event comprises a most recent transition between pairing states or a most recent decoding of an encoded information signal included in a detected ultrasonic beacon transmission.

15. The apparatus of claim 11, further comprising a motion sensor configured to detect motion of the apparatus;

wherein the processing unit is further configured to:

determine that the ultrasonic sensor detects, while the apparatus is operating in the first pairing state and after the threshold time of the pairing state initialization event, a second pilot signal included in a second ultrasonic beacon transmission that is subsequent to the first ultrasonic beacon transmission, the second ultrasonic beacon transmission further including a second encoded information signal;

determine that the motion sensor detects motion of the apparatus while the ultrasonic sensor detects the second pilot signal; and control, based on the determination that the motion sensor detects motion of the apparatus while the ultrasonic sensor detects the second pilot signal and without decoding the second encoded information signal, the apparatus to continue operating in the first pairing state.

16. A method comprising:

detecting, by an apparatus, a first pilot signal included in a first ultrasonic beacon transmission, the first ultrasonic beacon transmission further including a first encoded information signal;

decoding, by the apparatus and based on the first pilot signal, the first encoded information signal to identify a first medical system associated with the first ultrasonic beacon transmission;

entering, by the apparatus and based on the decoding of the first encoded information signal, into a first pairing state in which the apparatus is communicatively paired with the first medical system;

detecting, by the apparatus and while operating in the first pairing state and within a threshold time of entering the first pairing state, a second pilot signal included in a second ultrasonic beacon transmission, the second ultrasonic beacon transmission further including a second encoded information signal; and continuing, by the apparatus and based on the detection of the second pilot signal within the threshold time, operating in the first pairing state without decoding the second encoded information signal.

17. The method claim 16, further comprising:

determining, by the apparatus, that the apparatus does not detect any pilot signals within the threshold time and subsequent to the detection of the second pilot signal; and transitioning, by the apparatus and based on the determination that the apparatus does not detect any pilot signals within the threshold time and subsequent to the detection of the second pilot signal, from operating in the first pairing state to operating in a second pairing state that is different from the first pairing state.

18. The method claim 16, further comprising:

detecting, by the apparatus and while operating in the first pairing state and after the threshold time of entering the first pairing state, a third pilot signal included in a third ultrasonic beacon transmission, the third ultrasonic beacon transmission further including a third encoded information signal;

decoding, by the apparatus and based on the third pilot signal, the third encoded information signal to identify a medical system associated with the third ultrasonic beacon transmission;

determining, by the apparatus, that the medical system associated with the third ultrasonic beacon transmission corresponds to the first medical system; and continuing, by the apparatus and based on the determination that the medical system associated with the third ultrasonic beacon transmission corresponds to the first medical system, operating in the first pairing state.

19. The method claim 16, further comprising:

detecting, by the apparatus and while operating in the first pairing state and after the threshold time of entering the first pairing state, a third pilot signal included in a third ultrasonic beacon transmission, the third ultrasonic beacon transmission further including a third encoded information signal;

decoding, by the apparatus and based on the third pilot signal, the third encoded information signal to identify a medical system associated with the third ultrasonic beacon transmission;

determining, by the apparatus, that the medical system associated with the third ultrasonic beacon transmission corresponds to a second medical system that is different from the first medical system; and transition, by the apparatus and based on the determination that the medical system associated with the third ultrasonic beacon transmission corresponds to the second medical system, from operating in the first pairing state to operating in a third pairing state that is different from the first pairing state.

20. The method claim 16, further comprising:

detecting, by the apparatus and while operating in the first pairing state and after the threshold time of entering the first pairing state, a fourth pilot signal included in a fourth ultrasonic beacon transmission, the fourth ultrasonic beacon transmission further including a fourth encoded information signal;

determining, by the apparatus, that the fourth encoded information signal is not decodable;

determining, by the apparatus and based on the determination that the fourth encoded information signal is not decodable, that the apparatus is in motion while the apparatus detects the fourth pilot signal; and continuing, by the apparatus and based on the determination that the apparatus is in motion while the apparatus detects the fourth pilot signal, operating in the first pairing state without decoding the fourth encoded information signal.

\*  \*  \*  \*  \*